(12) United States Patent
Zinger et al.

(10) Patent No.: US 6,238,372 B1
(45) Date of Patent: May 29, 2001

(54) FLUID CONTROL DEVICE

(75) Inventors: Fredy Zinger, Ra'anana; Igor Denenburg, Rehovot, both of (IL)

(73) Assignee: Medimop Medical Projects Ltd., Ra'anana (IL)

( * ) Notice: Subject to any disclaimer, the term of this patent is extended or adjusted under 35 U.S.C. 154(b) by 0 days.

(21) Appl. No.: 08/913,432

(22) PCT Filed: Mar. 19, 1996

(86) PCT No.: PCT/US96/03732

§ 371 Date: Sep. 17, 1997

§ 102(e) Date: Sep. 17, 1997

(87) PCT Pub. No.: WO96/29113

PCT Pub. Date: Sep. 26, 1996

(30) Foreign Application Priority Data

Aug. 16, 1995 (IL) ........................................ 114960

(51) Int. Cl.[7] ...................................... A61M 5/00
(52) U.S. Cl. ........................ 604/246; 604/27; 604/32; 604/411
(58) Field of Search ............................... 604/32, 190, 248, 604/246, 411, 30; 137/625.41, 625.47

(56) References Cited

U.S. PATENT DOCUMENTS

| | | | |
|---|---|---|---|
| 4,253,501 | 3/1981 | Ogle | 141/27 |
| 4,638,975 | * 1/1987 | Iuchi et al. | 251/149.6 |
| 4,997,430 | * 3/1991 | Van Der Heiden et al. | 604/414 |
| 5,104,387 | * 4/1992 | Pokorney et al. | 604/248 |
| 5,288,290 | 2/1994 | Brody | 604/32 |
| 5,334,163 | * 8/1994 | Sinnett | 604/236 |

FOREIGN PATENT DOCUMENTS 0521460   1/1993   (EP) .

* cited by examiner

Primary Examiner—Sharon Kennedy
Assistant Examiner—Jennifer Maynard
(74) Attorney, Agent, or Firm—Ladas & Parry

(57) ABSTRACT

A fluid control device (10) for use with a syringe and at least one medicinal vessel (28). The fluid control device includes a first port (13), a second port (12) for receiving the syringe, a third port (17) including an adaptor (20) having a fluid conduit member (24) extending into the interior of the medicinal vessel (28) when attached thereto and a flow control member (20') selectively disposable from a first flow control position enabling a flow path between a first pair of two ports (12, 17) and second flow control position enabling a flow path between a second pair of two ports (12, 13). The flow control member (20') is coupled to one, of the ports for manipulation between its flow control positions.

9 Claims, 21 Drawing Sheets

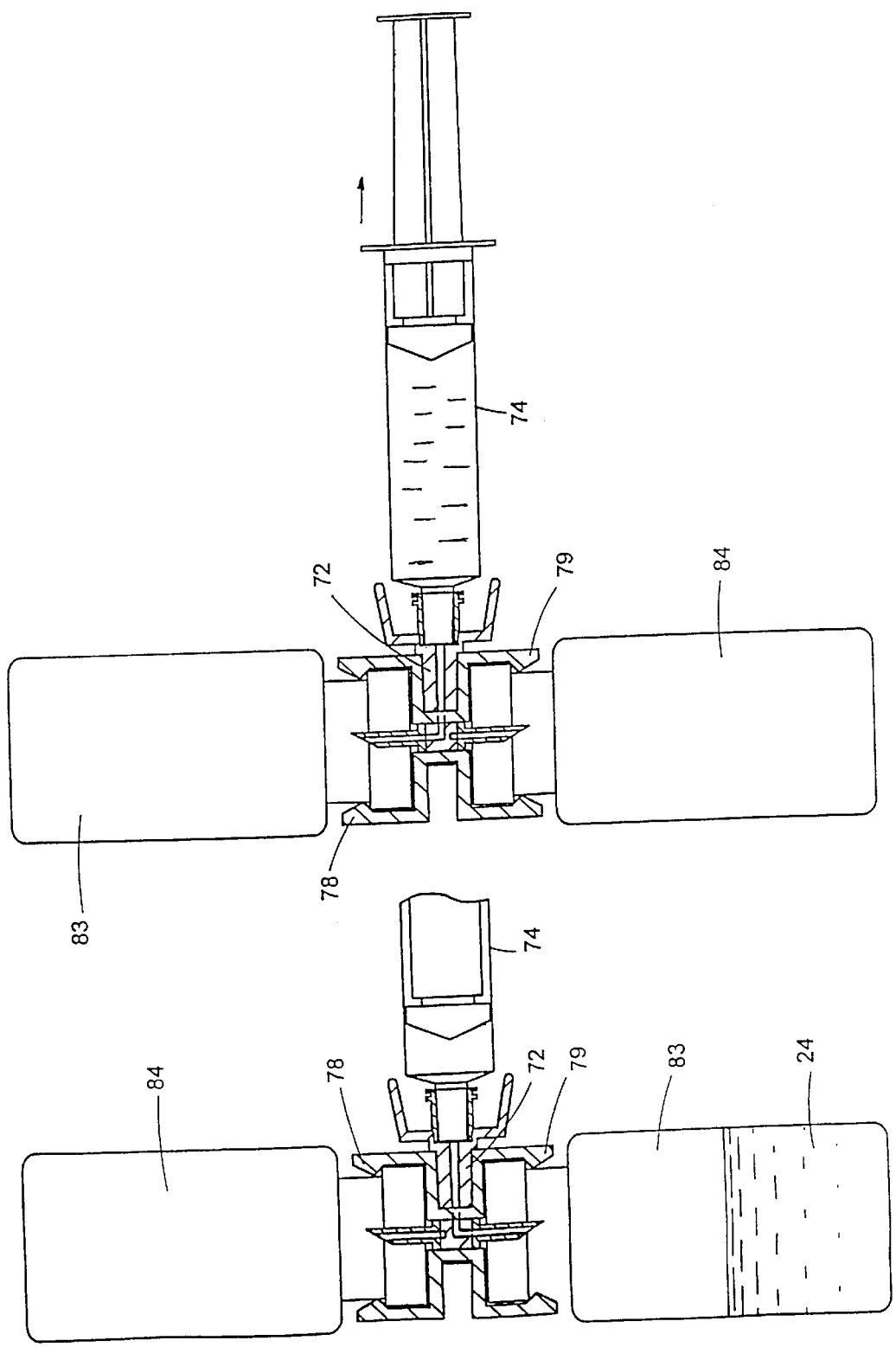

FLUID CONTROL DEVICE

This is a CIP of U.S. Application 08/499,213 filed Jul. 7, 1995, now abandoned, which is a CIP of 08/407,287 filed Mar. 20, 1995, now abandoned.

FIELD OF THE INVENTION

The invention relates to fluid control devices in general and in particular to fluid control devices adapted for facilitating the aseptic administration of drugs to patients.

BACKGROUND OF THE INVENTION

Drugs intended for parenteral administration are typically stored in a medicinal vessel either as a dry powder or as a solution. The solution can be ready for immediate use or in the form of a liquid concentrate which requires reconstitution with a physiological solution prior to administration in a similar manner to a dry powder drug. The physiological solution can be provided in a pre-filled syringe or a medicinal vessel.

Medicinal vessels typically fall into one of three categories. The first type is a vial or a glass bottle closed by a rubber stopper which can be penetrated by a puncturing tool, for example, a needle, and which is self-closing upon withdrawal of the puncturing tool. Such a vial or glass bottle can contain a single dose or a multiple dose of a drug. The drug contained in a vial can be under a high vacuum. The second type is an ampoule whose top portion is broken off enabling access to its contents. The third type is an IV bag provided with a sample port for enabling access to its contents. The sample port can be of the pre-slit septum type.

Regardless of the manner in which a drug is stored, there is a need to transfer fluid under sterile conditions before its administration to a patient by a dispensing tool be it a needle, a pre-slit septum, or the like. When a prior dilution of a drug is required, the process requires at least two fluid transfers. The problem of ensuring proper fluid transfer under aseptic conditions is especially acute in the case of self-administration of drugs by patients in their homes.

Assemblies which have hitherto been proposed for the aseptic administration of drugs are described in U.S. Pat. Nos: Des. 271,421, 3,618,637, 3,757,981, 3,826,261, 3,957, 052, 3,977,555, 3,993,063, 4,051,852, 4,564,054, 4,604,093, 4,721,133, 4,758,235, 4,967,797, 4,997,430, 5,201,705, 5,269,768, 5,279,576, 5,288,290, 5,334,163, and 5,466,220, and European Publication Nos: 0 258 913 A2, 0 195 018 B1, 0 192 661 B1, and 0 416 454 B1.

In particular, EP 0 521 460 B1 describes a fluid control device for use with a syringe and a pair of medicinal vessels. The fluid control device includes a housing with a Luer-connector port for receiving the syringe and second and third ports each comprising an adaptor having a fluid conduit member extending into the interior of a medicinal vessel when attached thereto. In the housing, a flow control member is slidingly displaceable from a first flow control position enabling a flow path between the two medicinal vessels when connected and a second flow control position enabling a flow path between one of the medicinal vessels and the syringe.

SUMMARY OF THE INVENTION

The object of the invention is to provide fluid control devices enabling the aseptic administration of drugs.

In accordance with the invention, there is provided a fluid control device for use with a syringe and at least one medicinal vessel, the fluid control device comprising:

(a) a first port;
(b) a second port for receiving the syringe;
(c) a third port comprising an adaptor having a fluid conduit member extending into the interior of the medicinal vessel when attached thereto; and
(d) a flow control member selectively disposable from a first flow control position enabling a flow path between a first pair of two ports and a second flow control position enabling a flow path between a second pair of two ports, said flow control member being coupled to one of said ports for manipulation between said flow control positions.

In accordance with the teachings of the present invention, there is provided a family of fluid control devices which are adapted for the aseptic administration of drugs either directly or indirectly to a patient. The selection of the most suitable fluid control device depends on the type of drug to be administered to a patient, the manner in which it is packaged, the manner in which it is to be administered to a patient and by whom apart from other factors. Some of the devices are designed to enable the reconstitution of a drug provided in a powder form or as a liquid concentrate. Some of the devices are suited for vials or ampoules containing a single dose of a drug whilst others are suited for vials or IV bags containing multiple doses.

In a preferred embodiment of a fluid control device, the flow control member is rotatably mounted in a body member so as to be selectively rotatable between its first flow control position and its second flow control position.

In a preferred embodiment of a fluid control device, the first port is adapted for dispensing a drug directly or indirectly to a patient and, as such, it can be provided with a needle, it can be fashioned as a male Luer connector on which a needle can be mounted or it can be fashioned as a plastic cannula for insertion into a pre-slit septum. In such an embodiment, the adaptor is preferably coupled to a flow control member adapted for rotation in a body member having the port adapted for receiving a syringe and the dispensing port.

The adaptor can be integrally formed with the flow control member and designed so as to readily broken off therefrom after rotation of the flow control member from its first flow control position to its second flow control position. Alternatively, the adaptor can be detachably engaged to the flow control member by means of an interengaging means enabling axial detachment of the adaptor from the body member on a relative rotation therebetween to a position which urges the flow control member from its first flow control position to its second flow control position.

In a preferred embodiment of a fluid control device suitable for use with drugs which require reconstitution, the fluid control device includes a fourth port in the form of an adaptor for enabling the attachment of a second medicinal vessel to the body member..

In a preferred embodiment of a fluid control device, the first port is also provided with an adaptor adapted for attachment thereto of a medicinal vessel and, in this case, the port adapted for receiving the syringe is rotatably coupled to the flow control member.

In each case, the adaptor can be adapted for attachment thereto of a vial, an ampoule or an IV bag, the former requiring that the fluid conduit member be formed as a puncturing tool for piercing the vial's rubber stopper on its attachment thereto. In the case of attachment of an ampoule, because the ampoule cannot be inverted, the fluid conduit member is required to be provided as a long straw to enable all or nearly all of its contents to be aspirated therefrom.

The adaptor can also include a conduit for venting the vessel when attached thereto. The conduit can include a filter for filtering the air traversing therethrough. The filter can be deployed within a lateral cavity provided within the adaptor or, alternately, the filter can be provided as a discrete element exterior to the fluid control device.

BRIEF DESCRIPTION OF THE DRAWINGS

For a better understanding of the present invention and to show how the same may be carried out in practice, and solely by way of non-limiting examples, reference will now be made to the accompanying drawings, in which.

DETAILED DESCRIPTION OF THE DRAWINGS

Figure 1:
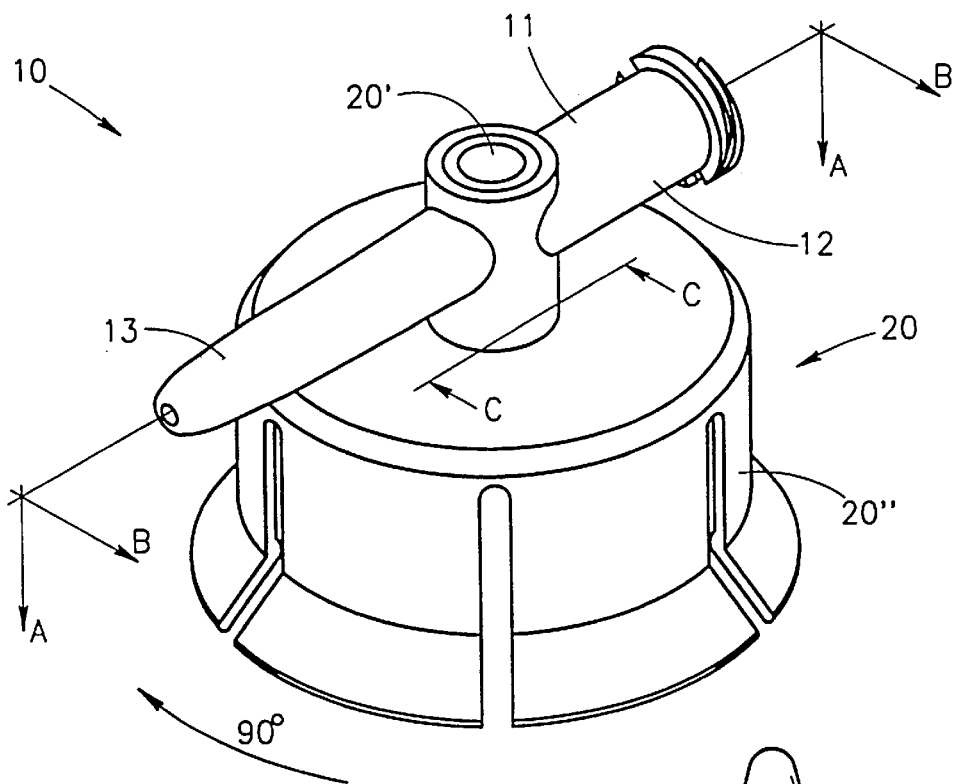
FIG. 1 is a perspective view of an assembled fluid control device including a base member and an integrally formed adaptor cum flow control member for use with a syringe and a medicinal vessel.
Figure 1:
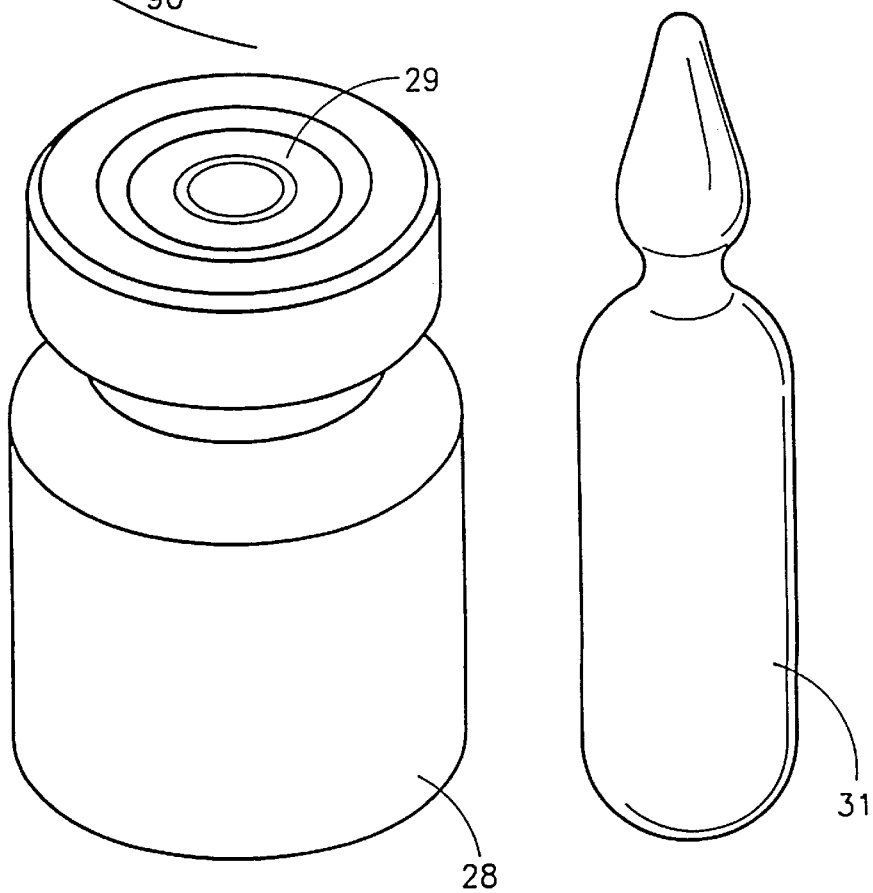
Figure 2:
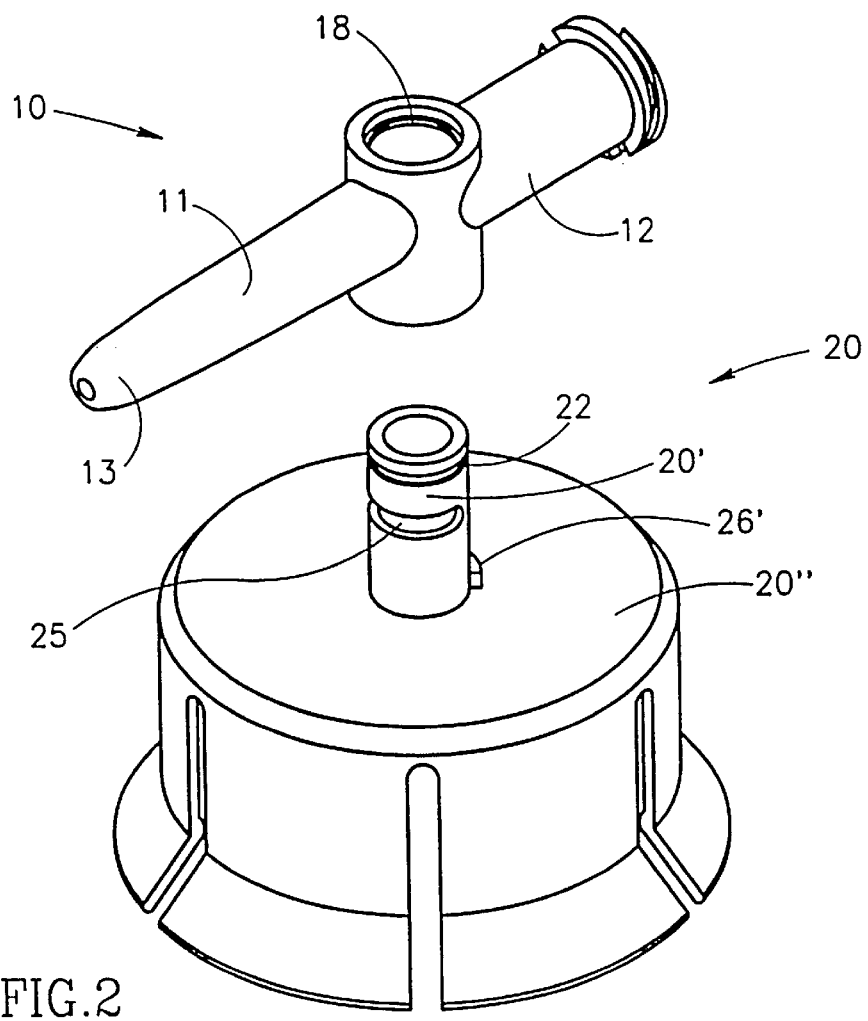
FIG. 2 is a perspective view of the fluid control device of FIG. 1 before assembly.

FIGS. 1–8 depict a first embodiment of a fluid, control device, generally designated 10, constructed and operative in accordance with the teachings of the present invention for enabling fluid flow control between a syringe, a medicinal vessel and a dispensing port. The fluid control device 10 includes an elongated base member 11 having a port. 12 adapted for receiving a syringe and a dispensing port 13 fashioned as a plastic cannula for insertion into a pre-slit septum assembly known in the art per se. The port 12 is typically fashioned as a female Luer connector.

Figure 3:
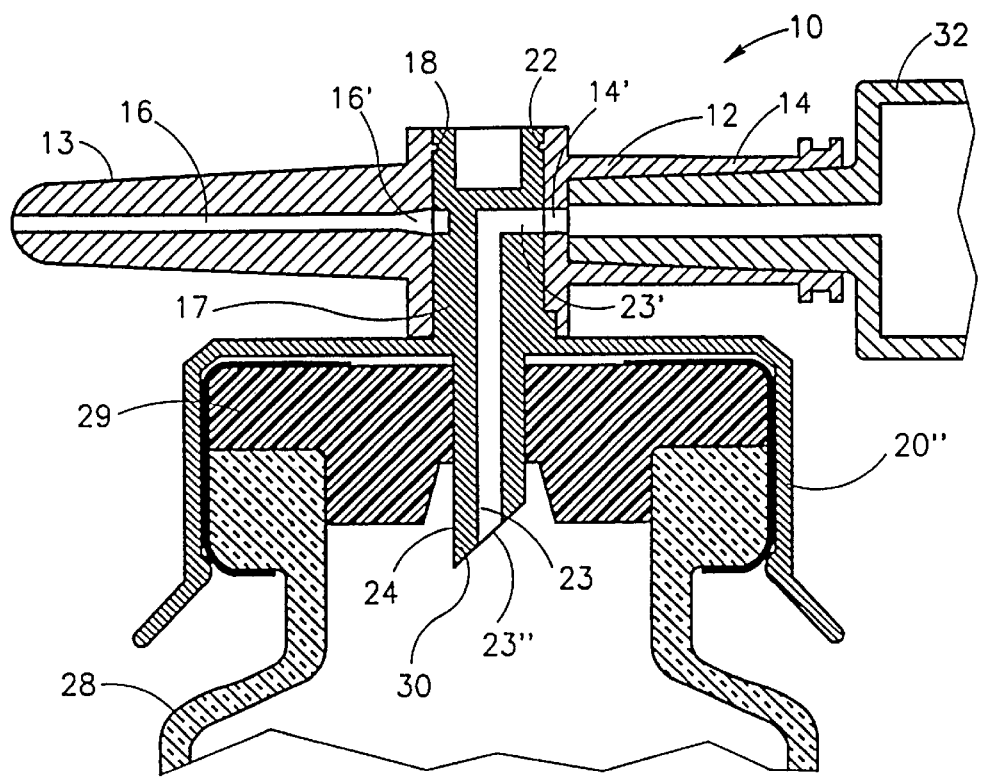
FIG. 3 is a vertical cross sectional view of the fluid control device of FIG. 1 along the line A—A after insertion of a syringe and the attachment of a vial and before rotation of the adaptor relative to the base member.

As shown in FIG. 3, the port 12 includes a lumen 14 having an interior opening 14' and the dispensing port 13 includes a lumen 16 having an interior opening 16'. The lumens 14 and 16 are co-axial and in flow communication via a bore 17 transversely disposed relative to the elongated base member 11. The bore 17 includes an upper peripheral flange 18 and a lower minor peripheral abutment wall portion 19' protruding radially inward relative to its major peripheral wall portion 19" (see FIG. 5). As shown, the abutment wall portion 19' typically extends through an arc angle of about 90°.

The fluid control device 10 further includes an integrally formed adaptor cum flow control member, generally designated 20, for insertion into the bore 17 in which it is restrained therein by means of a peripherally formed groove 22 designed for receiving the flange 18 therein. The flow control member 20' is formed with two flow ducts as follows: A first flow duct 23 (see FIG. 3) in the form of an L-shaped channel having a radial aperture 23' for registration with the interior opening 14' and an axial aperture 23' of a fluid conduit member 24 integrally formed as part of the adaptor 20" on disposition of the flow control member 20' in a first flow control position enabling flow communication between a syringe inserted in the port 12 and a vessel attached to the adaptor 20". A second flow duct 25 (see FIG. 4) in the form of a peripheral slightly longer than a semi-circular groove 25 having a first end portion 25' for registration with one of the interior openings 14' and 16' and a second end portion 25" for registration with the other of the interior openings 14' and 16' on disposition of the flow control member 20' in a second flow control position enabling flow communication between a syringe inserted in the port 12 and the dispensing port 13.

Figure 5:
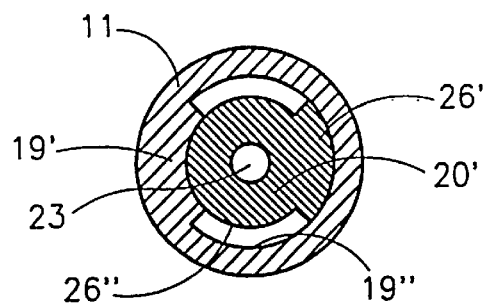
FIG. 5 is a horizontal cross sectional view of the fluid control device of FIG. 1 along the line C—C before rotation of the adaptor relative to the base member.

In addition, the flow control member 20' is provided with a minor peripheral abutment wall portion 26' protruding radially outward relative to its major peripheral wall portion 26" (see FIG. 5). As shown, the abutment wall portion 26' typically extends through an arc angle of about 90°. The minor peripheral abutment wall portions 19' and 26' are so disposed such that they assume substantially diagonally opposing positions relative to one another (see FIG. 5) in the first flow control position of the flow control member 20'.

The adaptor 20" is shown to be adapted for the attachment thereto of a vial 28 (not drawn to size) provided with a rubber stopper 29. As such, the fluid conduit member 24 is fashioned as a puncturing tool 30 for penetrating a rubber stopper 29 on attachment of a vial 28 to its adaptor 20". Alternatively, the adaptor 20" can be adapted for the attachment thereto of an ampoule 31 (not drawn to size), the difference being that such an adaptor will preferably have relatively long springy grips.

Each stage of the two stage operation of the fluid control device 10 for the administration of a drug provided in powder form for dilution with a physiological solution provided in a pre-filled syringe is now described with reference to FIGS. 3–5 and FIGS. 6–8, respectively.

Figure 4:
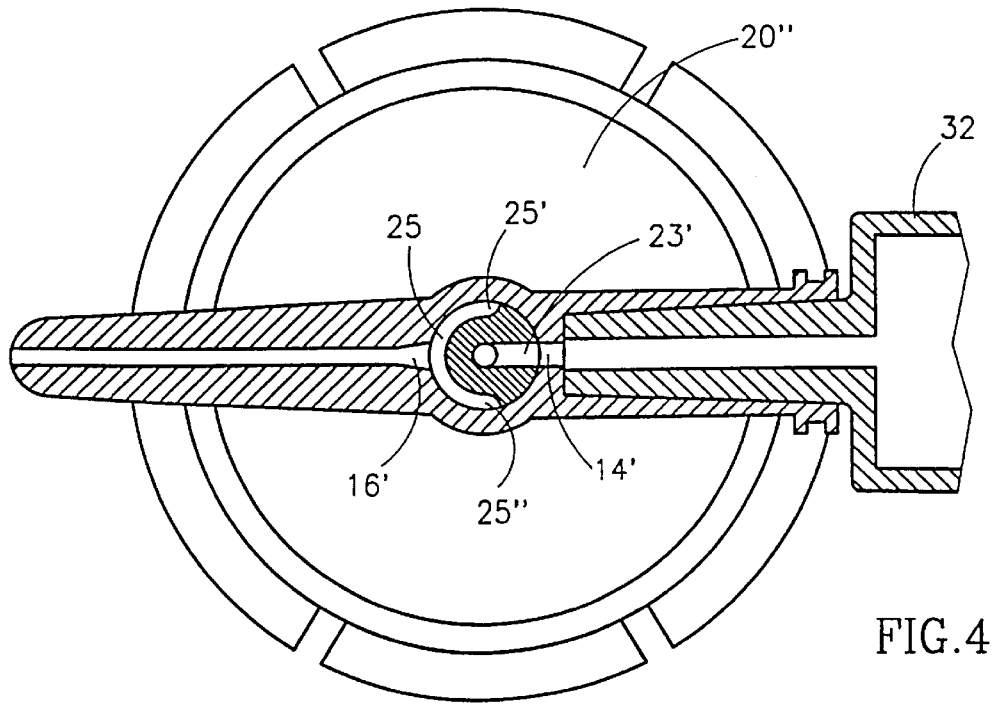
FIG. 4 is a horizontal cross sectional view of the fluid control device of FIG. 1 along the line B—B after insertion of a syringe and the attachment of a vial and before rotation of the adaptor relative to the base member.

As shown in FIGS. 3–5, the fluid control device 10 is best provided in a set-up position in which the flow control member 20' is in its first flow control position and the two minor abutment wall portions 19' and 26' are diagonally opposed to one another. As shown, it should be noted as best seen in FIG. 4, that the semi-circular groove 25 registers with the interior opening 16' but does not provide a flow path.

In this arrangement, a pre-filled syringe 32 is inserted into the port 12 and the vial 28 is attached to the adaptor 20" by means of which action, the puncturing tool 30 punctures the vial's rubber stopper 29, thereby enabling flow communication with its interior via the fluid conduit member 24. Typically, the syringe 32 requires actuation for expressing its contents into the vial 28 whilst, in some cases, if the contents of the vial 28 are under vacuum, then the physiological solution of the syringe 32 can be sucked into the vial without user intervention. Thereafter, the contents of the vial 28 are shaken so as to reconstitute the powdered drug. The fluid control device 10 together with the vial 28 are then preferably inverted and the syringe 32 is aspirated so as to draw the reconstituted liquid drug thereinto.

Figure 6:
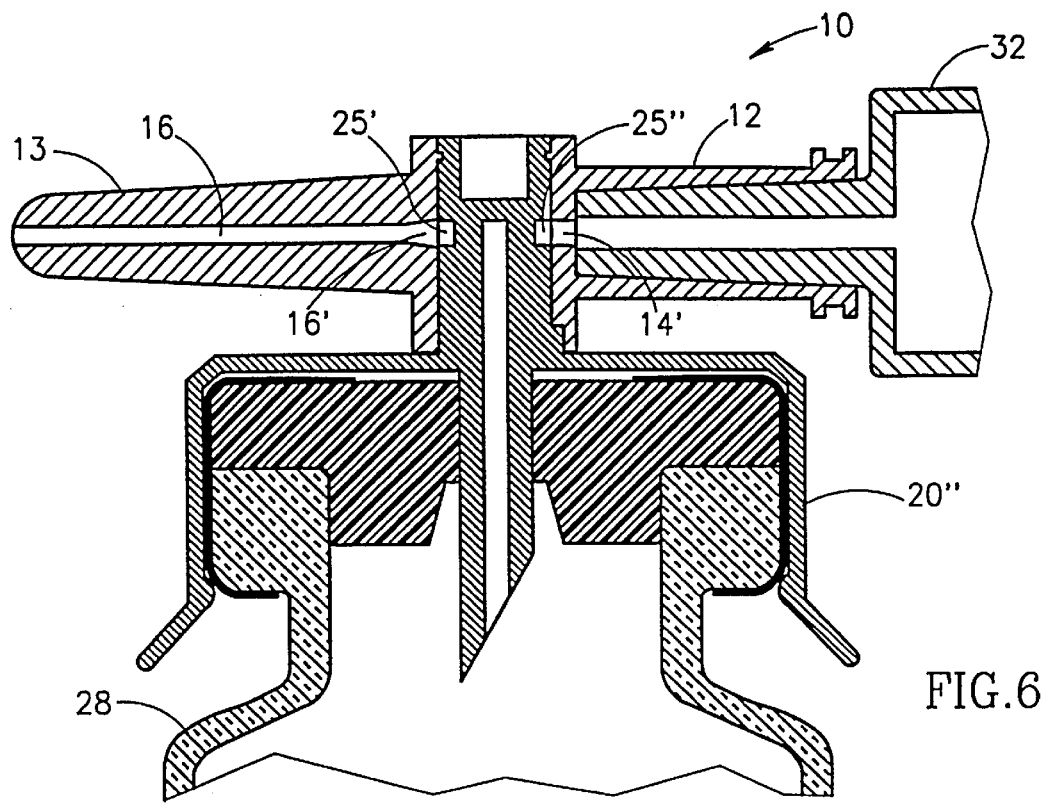
FIG. 6 is a vertical cross sectional view of the fluid control device of FIG. 1 along the line A—A after rotation of the adaptor relative to the base member.
Figure 7:
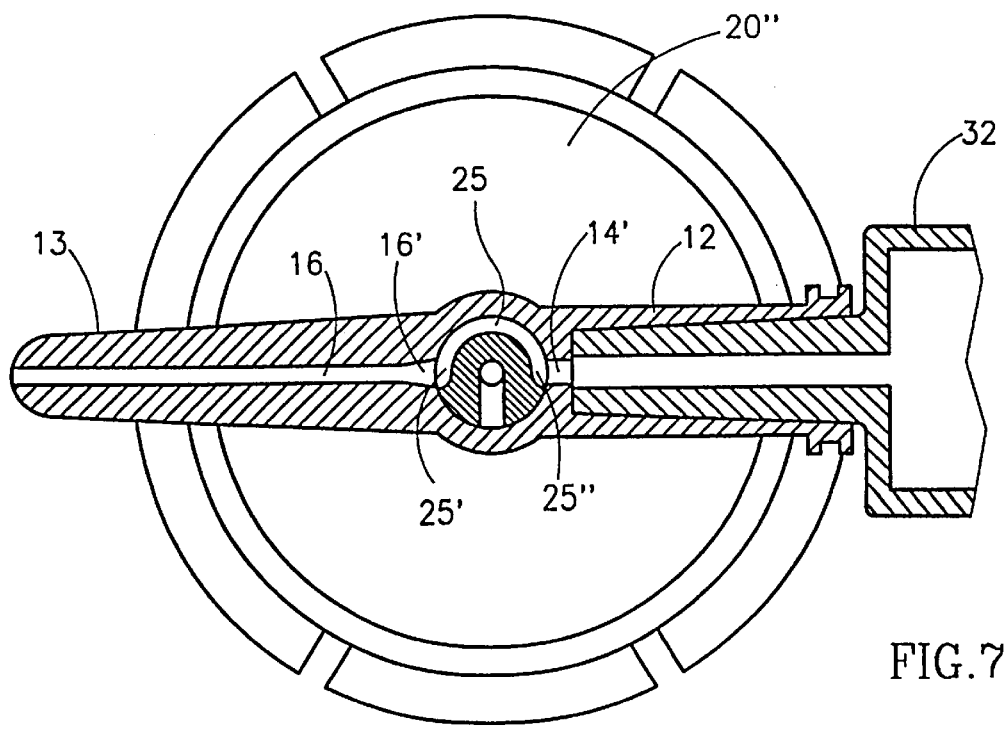
FIG. 7 is a horizontal cross sectional view of the fluid control device of FIG. 1 along the line B—B after rotation of the adaptor relative to the base member.
Figure 8:
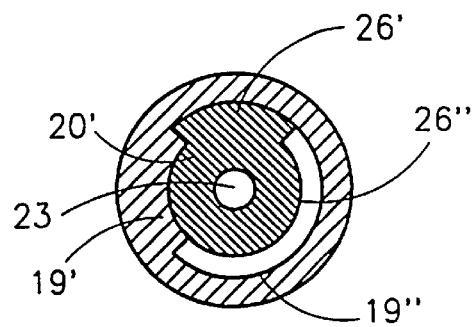
FIG. 8 is a horizontal cross sectional view of the fluid control device of FIG. 1 along the line C—C before rotation of the adaptor relative to the base member.

Turning now to FIGS. 6–8; the vial 28 together with the adaptor 20" are rotated in either a clockwise or a counter clockwise direction relative to the base member 11 until such time that abutment wall portion 26' is stopped by the abutment wall portion 19' (see FIG. 8). On rotation of the adaptor 20", the flow control member 20' is rotated to its second flow control position enabling a flow path between the syringe 32 and the dispensing port 13 by means of the end portions 25' and 25" of the semi-circular groove 25 registering with the interior openings 14' and 16'. The drug can then be dispensed by actuation of the syringe 32.

It can now be readily appreciated that the fluid control device 10 ensures that a drug can be administered to a patient under aseptic conditions. Furthermore, it can be readily appreciated that the fluid control device 10 presents a "fool-proof" delivery device in the sense that a patient is required to perform a minimal number of actions to administer a drug and that the drug can only be dispensed in a single operative position of the fluid control device.

Figure 9:
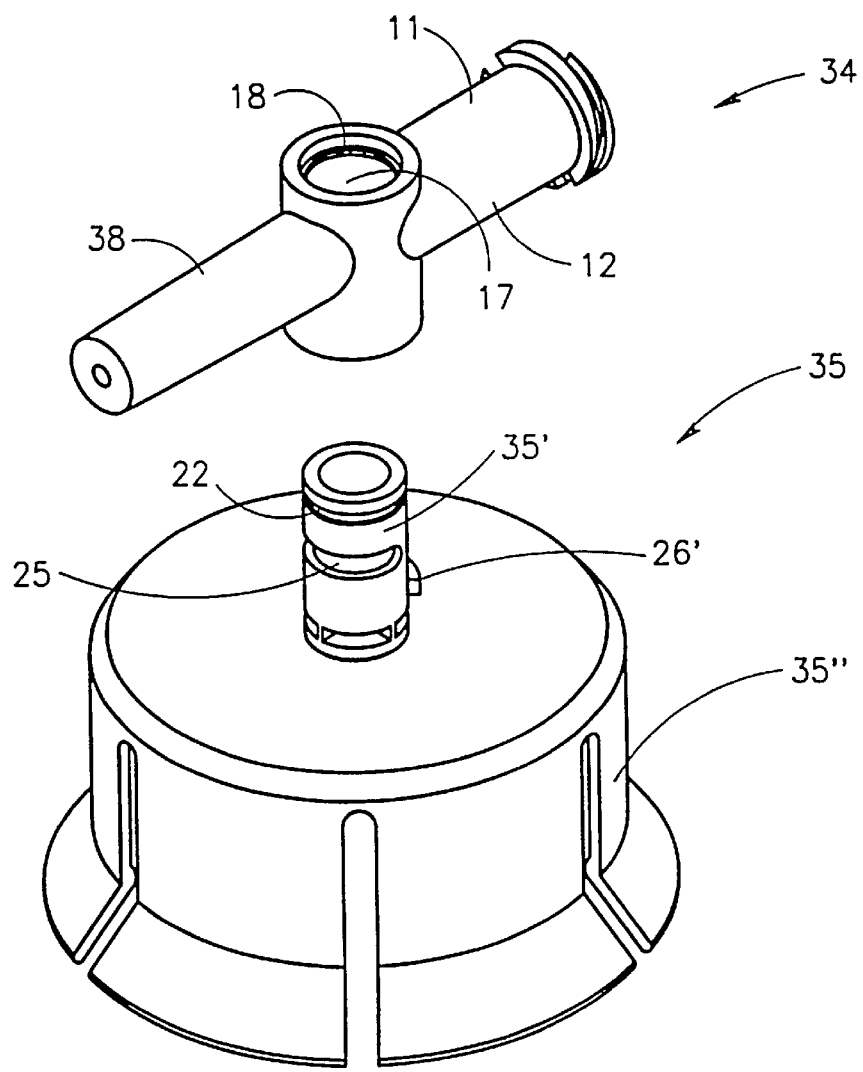
FIG. 9 is a perspective view of a modified integrally formed adaptor cum flow control member adapted such that the adaptor breaks off from the flow control member on rotation of the adaptor relative to the base member beyond a pre-determined position.
Figure 10:
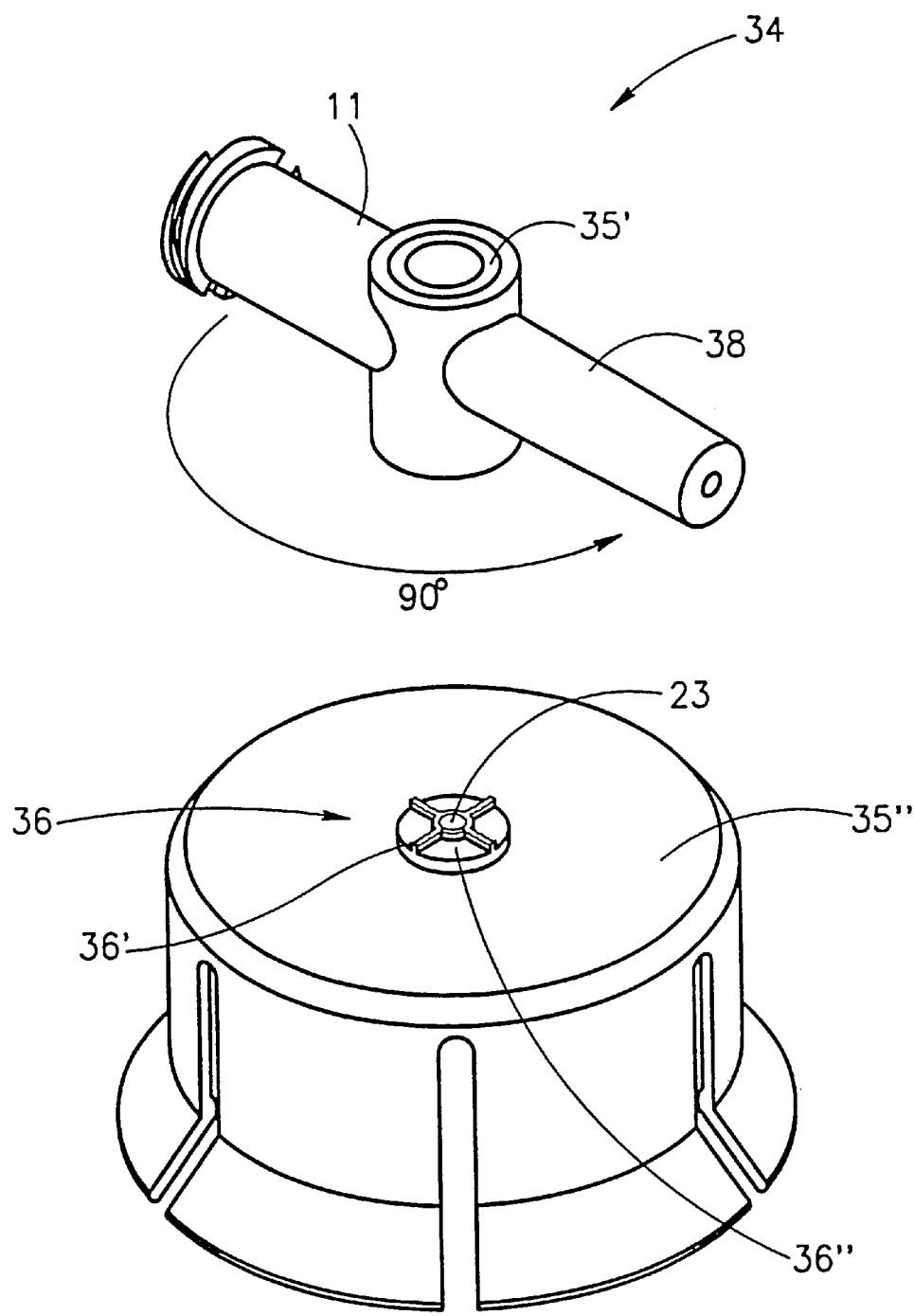
FIG. 10 is a perspective view of a fluid control device including the modified adaptor cum flow control member of FIG. 9 after the adaptor has been broken off.
Figure 11:
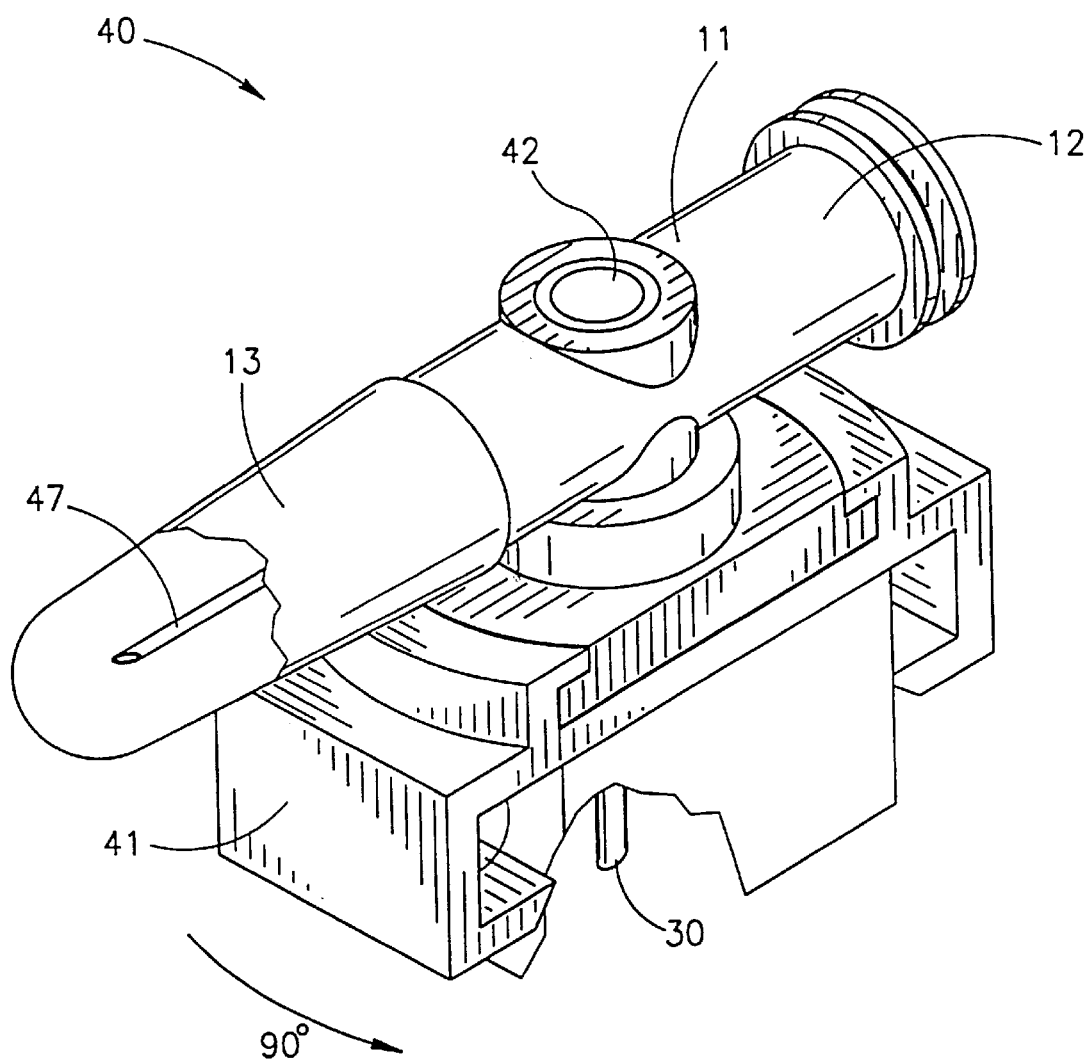
FIG. 11 is a perspective view of an assembled fluid control device including a base member and an adaptor designed for releasable engagement with the base member.
Figure 12:
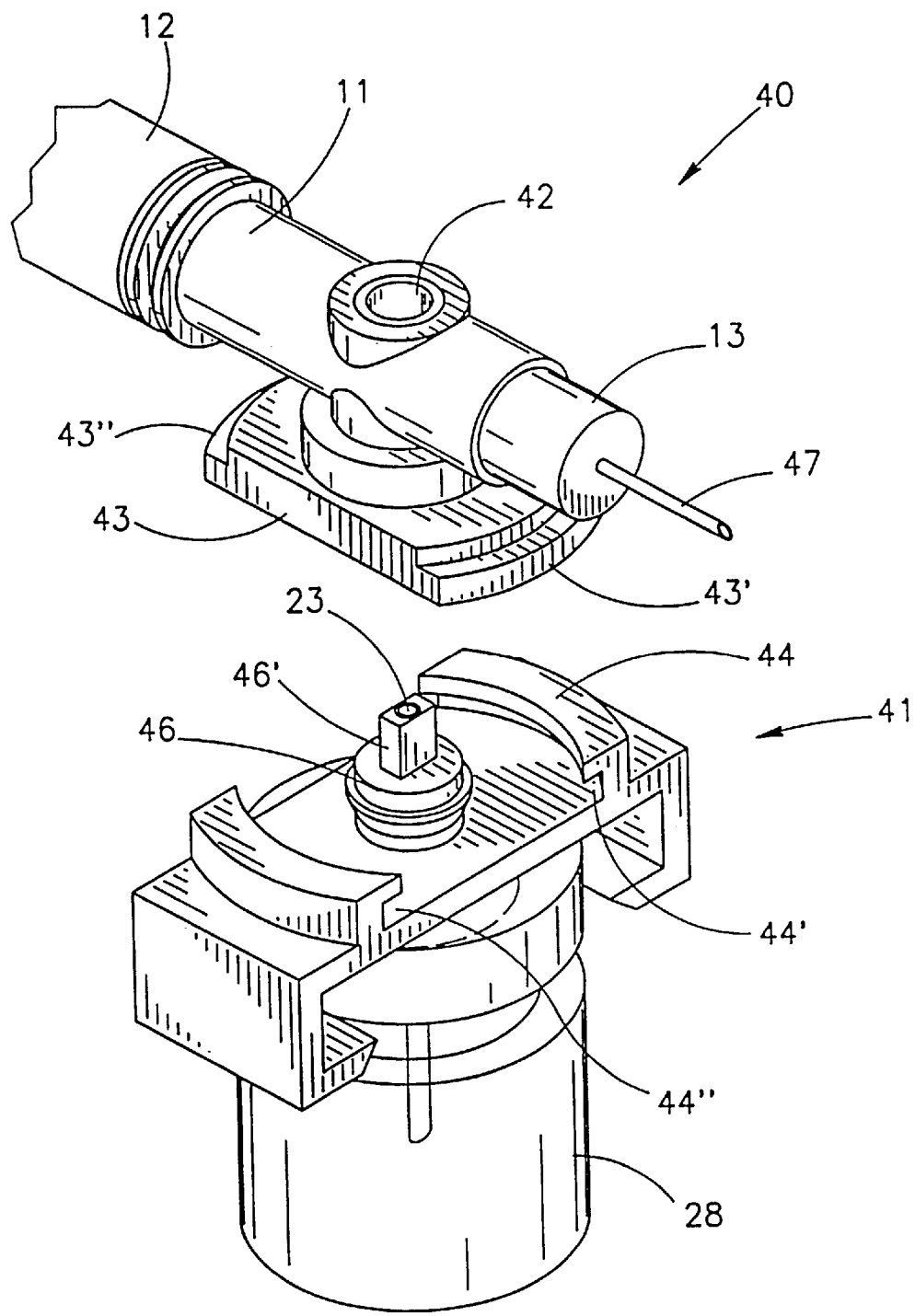
FIG. 12 is a perspective view of the fluid control device of FIG. 11 after the adaptor has been rotated through a quarter turn ready for its detachment from the base member.

FIGS. 9 and 10 depict a second embodiment of a fluid control device, generally designated 34, constructed and operative in accordance with the teachings of the present invention for enabling fluid flow control between a syringe, a medicinal vessel and a dispensing port. The fluid control device 34 is similar in construction and operation to the fluid control device 10 and therefore the same reference numbers are used where appropriate.

The main difference between the two fluid control devices 34 and 10 resides in the fact that the former includes an integrally formed adaptor cum flow control member 35 provided with a weakened portion, generally designated 36, between its abutment wall portion 26' of its flow control member 35' and its adaptor 35". As shown, this weakened portion 36 is achieved by leaving radially extending vanes 36' formed by cut-outs 36".

The advantage of this design is that after rotation of the vial 28 (not shown) and the adaptor 35" through 90° so as to rotate the flow control member 35' from its first flow control position to its second flow control position, any further torque applied will tend to snap off the adaptor 35" which can then be discarded together with the vial, thereby rendering a less cumbersome and lighter remaining assembly so as to facilitate the administration of a drug.

A further difference between the fluid control devices 34 and resides in the fact the former includes a dispensing port 38 fashioned as a male Luer connector.

Figure 13:
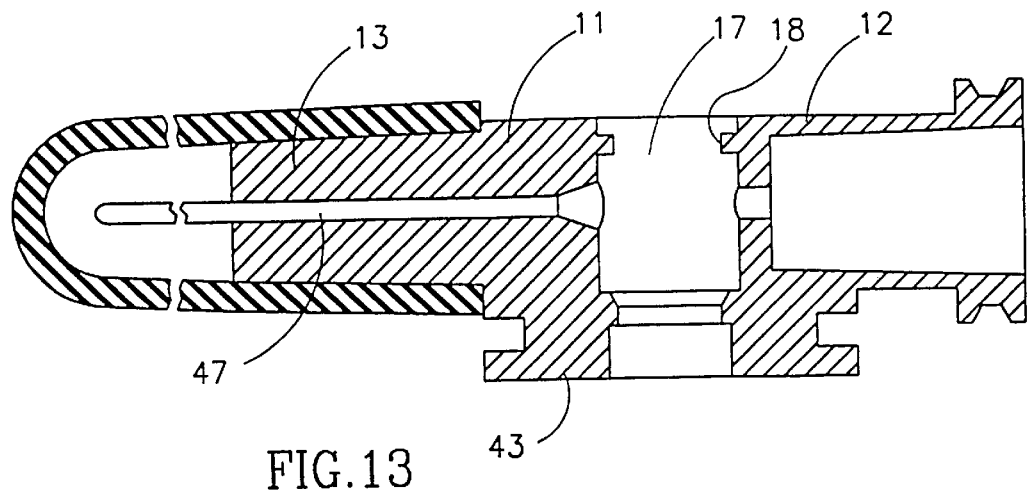
FIG. 13 is a vertical cross sectional view of the base member of the fluid control device of FIG. 11.
Figure 14:
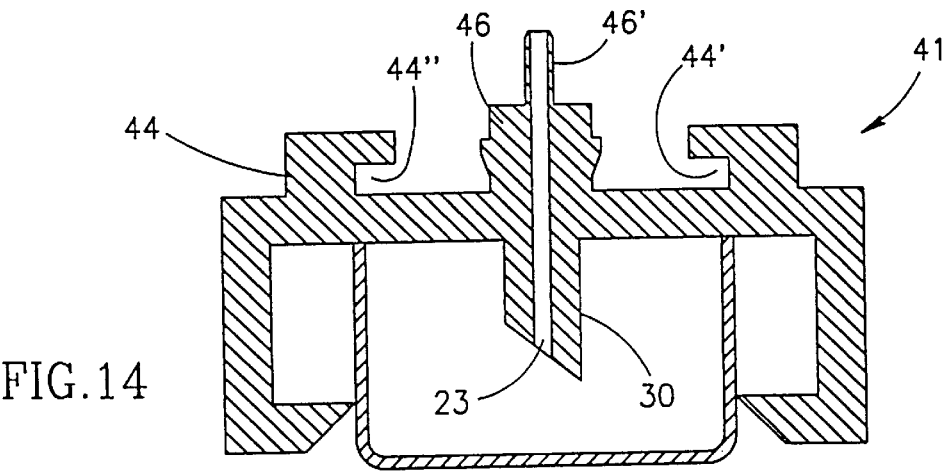
FIG. 14 is a vertical cross sectional view of the adaptor of the fluid control device of FIG. 11.
Figure 15:
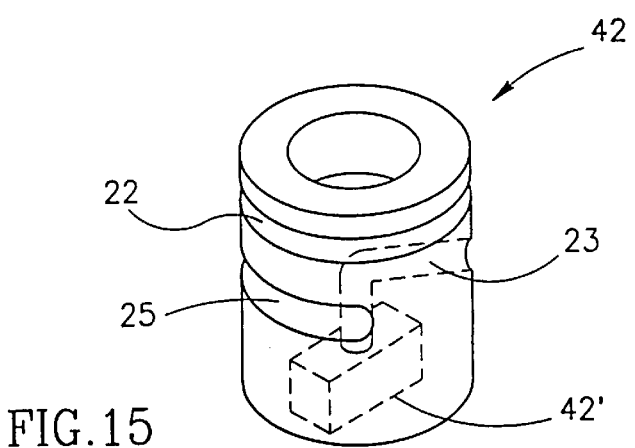
FIG. 15 is a perspective view of the flow control member of the fluid control device of FIG. 11.

FIGS. 13–15 depict a third embodiment of a fluid control device, generally designated 40, constructed and operative in accordance with the teachings of the present invention for enabling fluid flow control between a syringe, a medicinal vessel and a dispensing port. The fluid control device 40 is similar in construction and operation to the fluid control device 10 and therefore the same reference numerals are used where appropriate.

The main difference between the two fluid control devices 40 and 10 resides in the fact that the former includes an adaptor 41 designed for a non-destructive detachable engagement with a flow control member 42. As such, the base member 11 is provided with a downwardly depending rectangular shaped skirt 43 provided with outwardly extending flanges 43' and 43" for engagement by an upwardly extending rectangular shaped grip 44 of the adaptor 41 provided with inwardly directed grooves 44' and 44" for receiving the flanges 43' and 43". In addition, the adaptor 41 is provided with an upwardly extending stem 46 provided with a rectangular shaped key 46' for insertion into a similarly sized and shaped slot 42' formed in the underside of the flow control member 42.

In the fluid control device 40, the flow control member 42 is disposed in its first flow control position enabling a flow path between the port 12 and a medicinal vessel to be attached to the adaptor 41 when the adaptor 41 is mounted on the base member 11. Conversely, on the rotation of the adaptor 41 relative to the base member 11 to a position enabling axial detachment therefrom, the adaptor 41 urges the flow control member 42 from its first flow control position to its second flow control position enabling a flow path between the port 12 and the dispensing port 13. Preferably, there is a screw thread engagement between the base member 11 and the adaptor 41 designed such that there is an axial displacement of the adaptor 41 away from the base member 11 when it is rotated from its engaging position to its disengaging position.

It can be readily appreciated that the advantage of this design over the design of the fluid control device 34 whilst retaining all the advantages of the latter resides in the fact that the former is reusable after sterilization whilst the latter can only be used once due to the destruction of the adaptor cum flow control member 35.

A further difference between the fluid control devices 40 and 10 resides in the fact the former includes a dispensing port 13 provided with a needle 47.

Figure 16A:
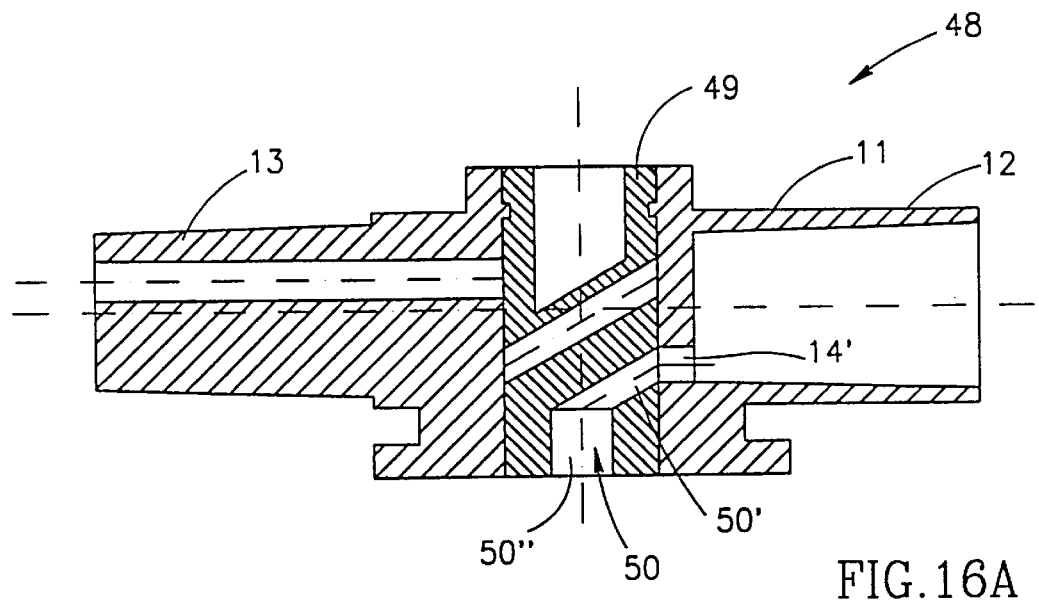
FIGS. 16A and 16B are vertical cross sectional views of a fluid control device in which the flow control member is required to be rotated through 180° to enable switching between its flow control position.
Figure 16B:
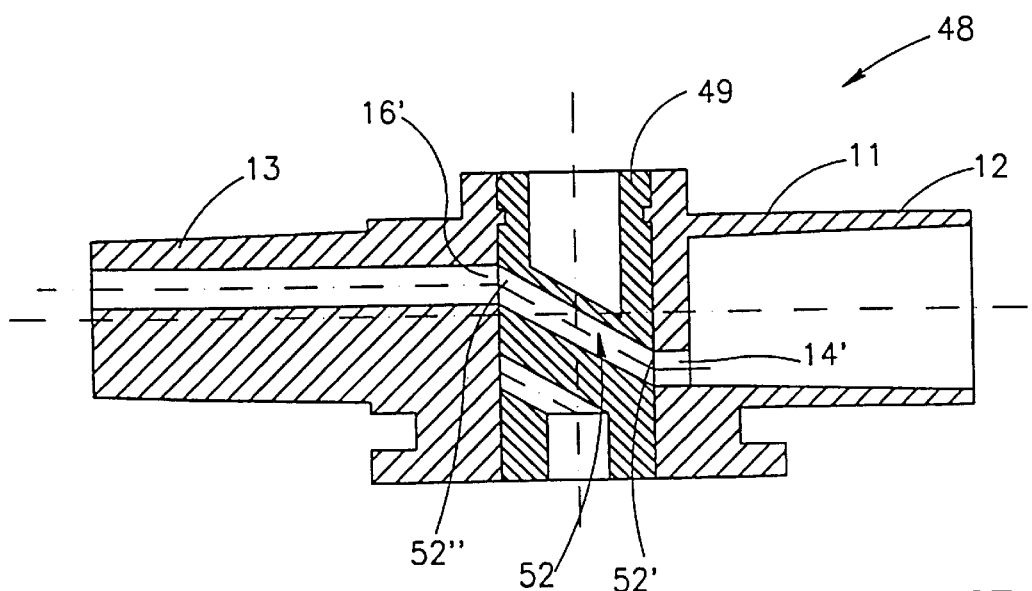

FIGS. 16A and 16B depict a fourth embodiment of a fluid control device, generally designated 48, constructed and operative in accordance with the teachings of the present invention for enabling fluid flow control between a syringe, a medicinal vessel and a dispensing port. The fluid control device 48 is similar in construction and operation to the fluid control device 41 and therefore the same reference numerals are used where appropriate.

The main difference between the two fluid control devices 48 and 41 resides in the fact that the former includes a flow control member 49 which is required to be rotated through a 180° turn between its first flow control position (see FIG. 16A) and its second flow control position (see FIG. 16B). In particular, the flow control member 49 includes an inclined channel 50 having a radial aperture 50' for registration with the interior opening 14' and an axial aperture 50" for registration with the fluid conduit member 24 so as to enable the flow path between a syringe and the interior of a medicinal vessel. And, the flow control member 49 includes a second inclined channel 52 having a radial aperture 52' for registration with the interior opening 14' and a radial aperture 52" for registration with the interior opening 16' so as to enable the flow path between a syringe to the dispensing port 13. As shown, in this case, the lumens 14 and 16 are not co-axial.

Figure 17:
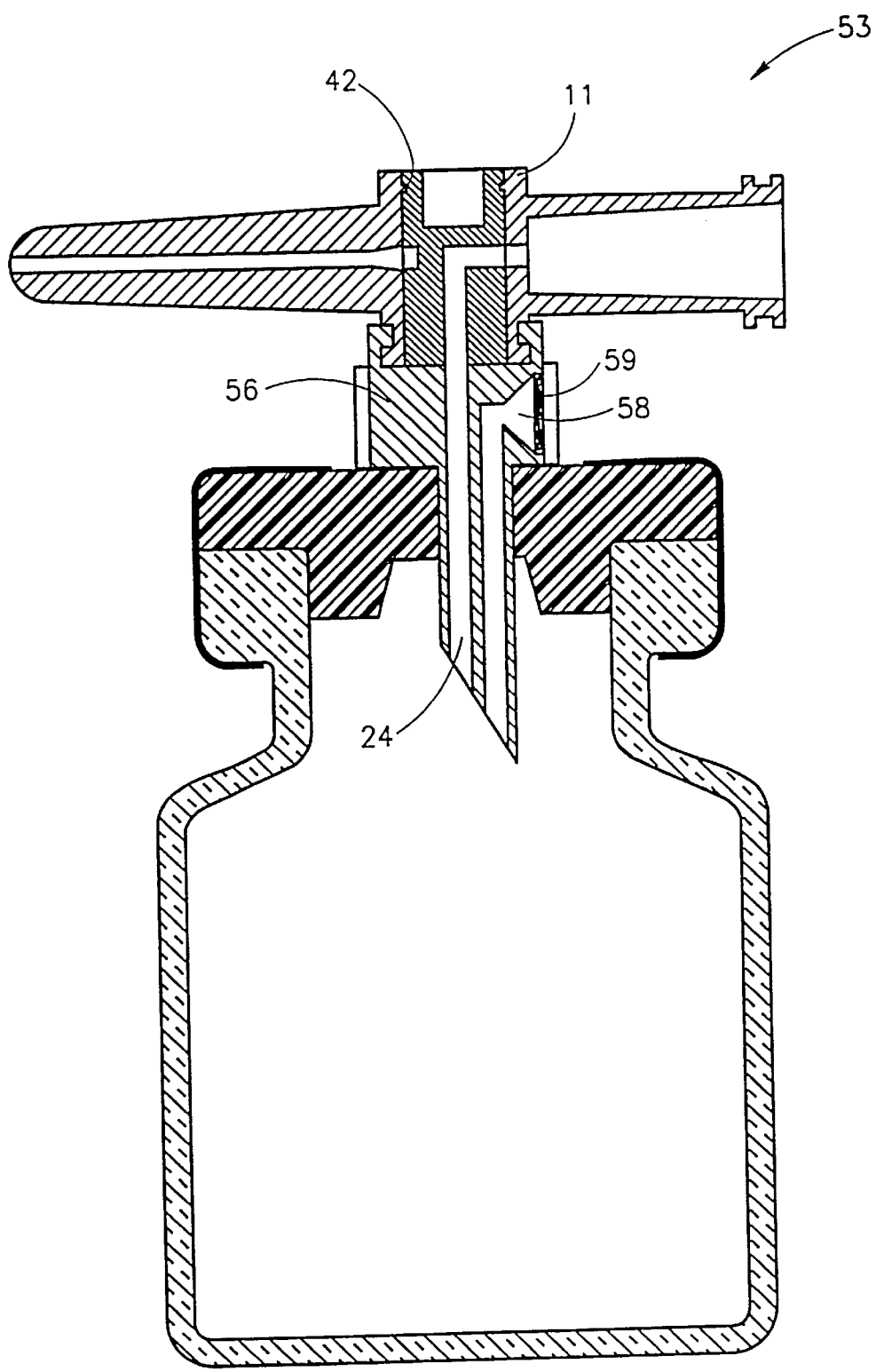
FIG. 17 is a vertical cross sectional view of a fluid control device provided with an arrangement for the venting of a vial attached to its adaptor.
Figure 18A:
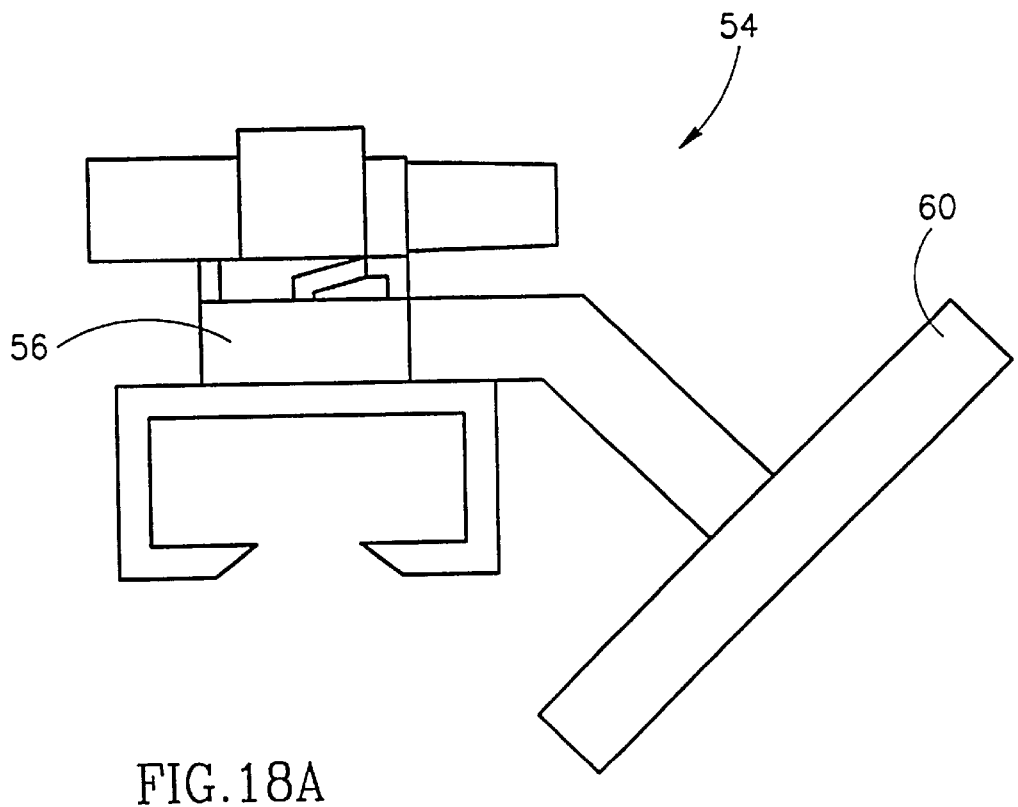
FIGS. 18A and 18B are two views depicting a fluid control device having a filter for filtering air venting a vial attached to its adaptor, the filter being provided as a discrete element exterior to the device.
Figure 18B:
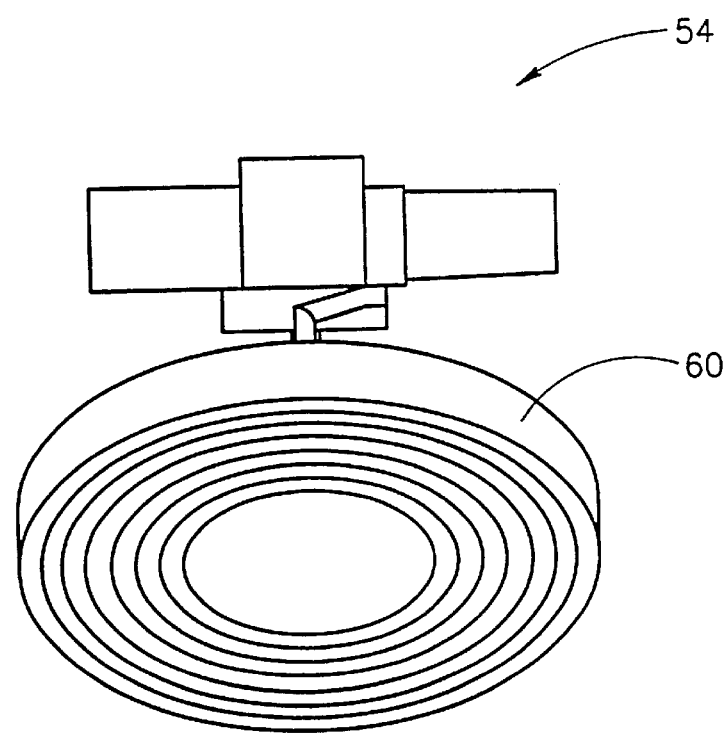
Figure 19:
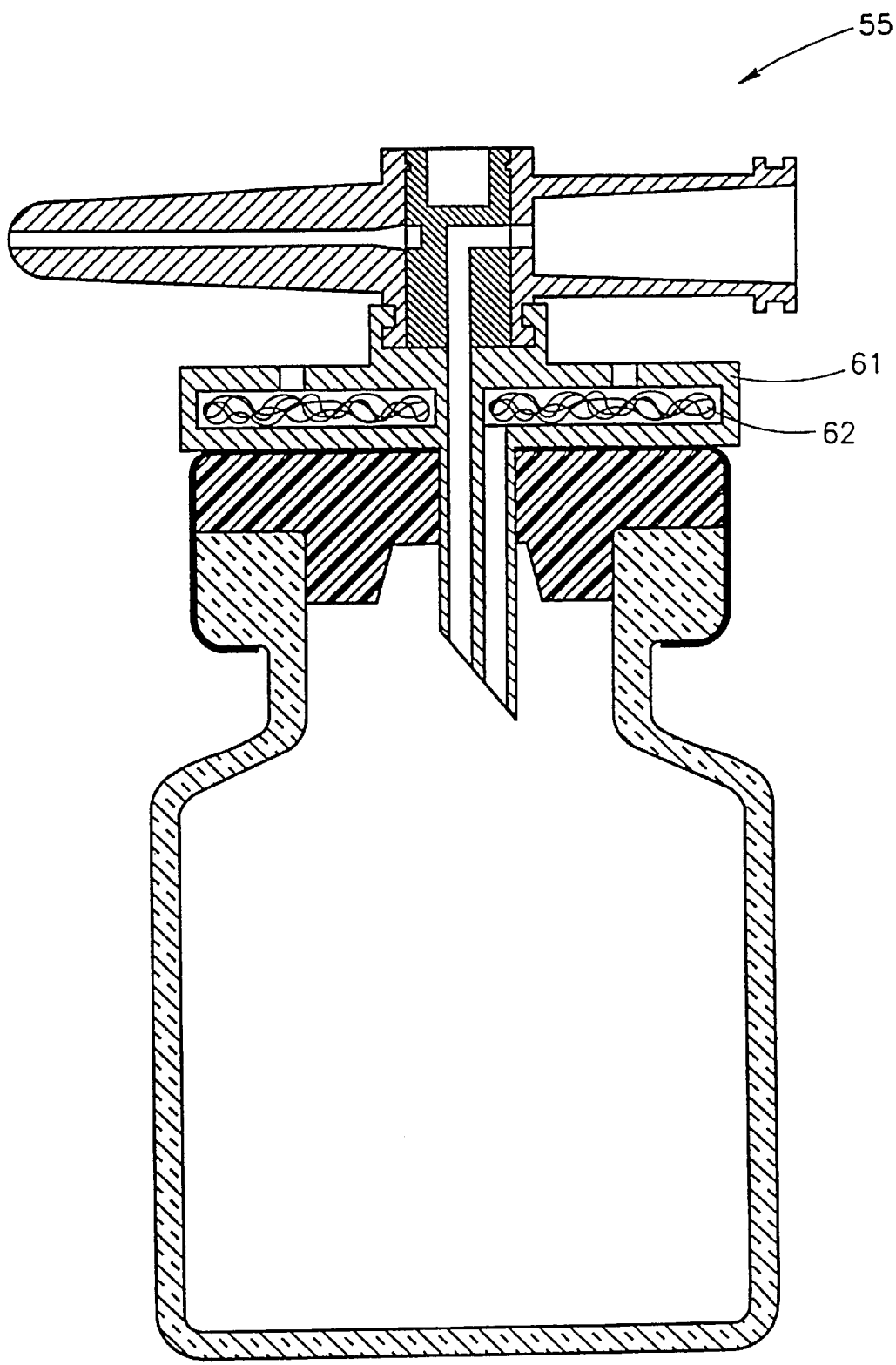
FIG. 19 is a vertical cross sectional view of a fluid control device having an adaptor provided with a lateral cavity for receiving a filter for filtering air venting a vial attached thereto.

FIGS. 17–19 depict other modified fluid control devices, generally ' designated 53, 54 and 55, constructed and operative in accordance with the teachings of the present invention for enabling fluid flow control between a syringe, a medicinal vessel and a dispensing port The fluid control device 53, 54 and 55 are similar in construction and operation to the fluid control device 41 and therefore the same reference numerals are used where appropriate. The main difference between the fluid control devices 53, 54 and 55 and the fluid control device 41 is that they provide arrangements for venting a vial and, if necessary, for filtering incoming air.

Turning now to FIG. 17, the fluid control device 53 includes an adaptor 56 provided with a venting conduit 58 for venting a vial 28 to the atmosphere in addition to the fluid conduit member 24. The venting conduit 58 is preferably provided with a filter 59 for filtering incoming air. Turning now to FIGS. 18a and 18b, the fluid control device 54 is similar to the fluid control device 53 except that it includes a filter 60 exterior to the adaptor 56. Turning now to FIG. 19, the fluid control device 55 is similar to the fluid control device 53 except that its adaptor 61 includes an integrally formed laterally disposed filter 62.

Figure 20:
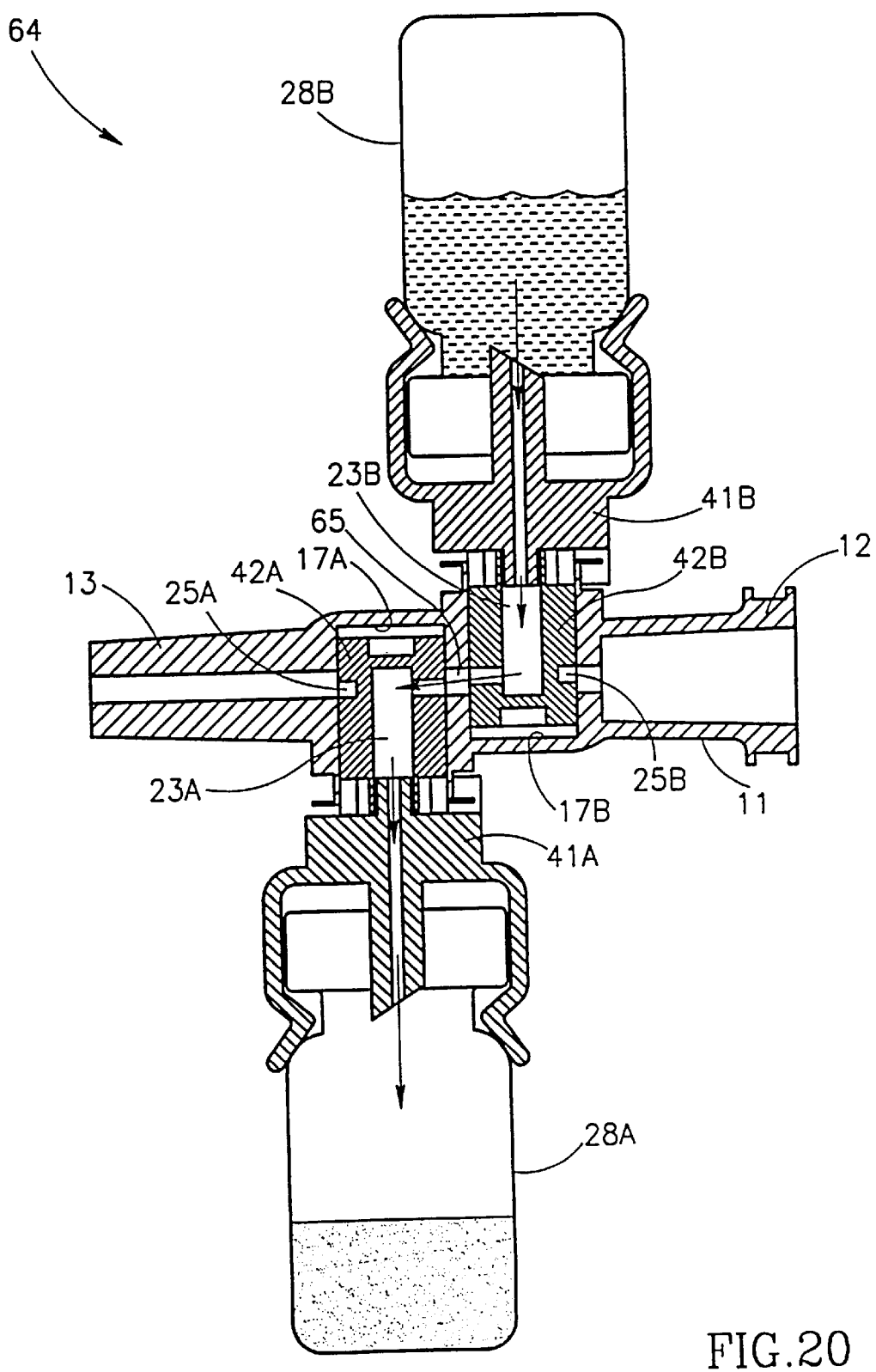
FIG. 20 is a vertical cross-sectional view of a fluid control device in a first operative position enabling flow communication between a medicinal vessel containing a powder drug and a medicinal vessel containing a physiological solution for enabling reconstitution of the powder drug.
Figure 21:
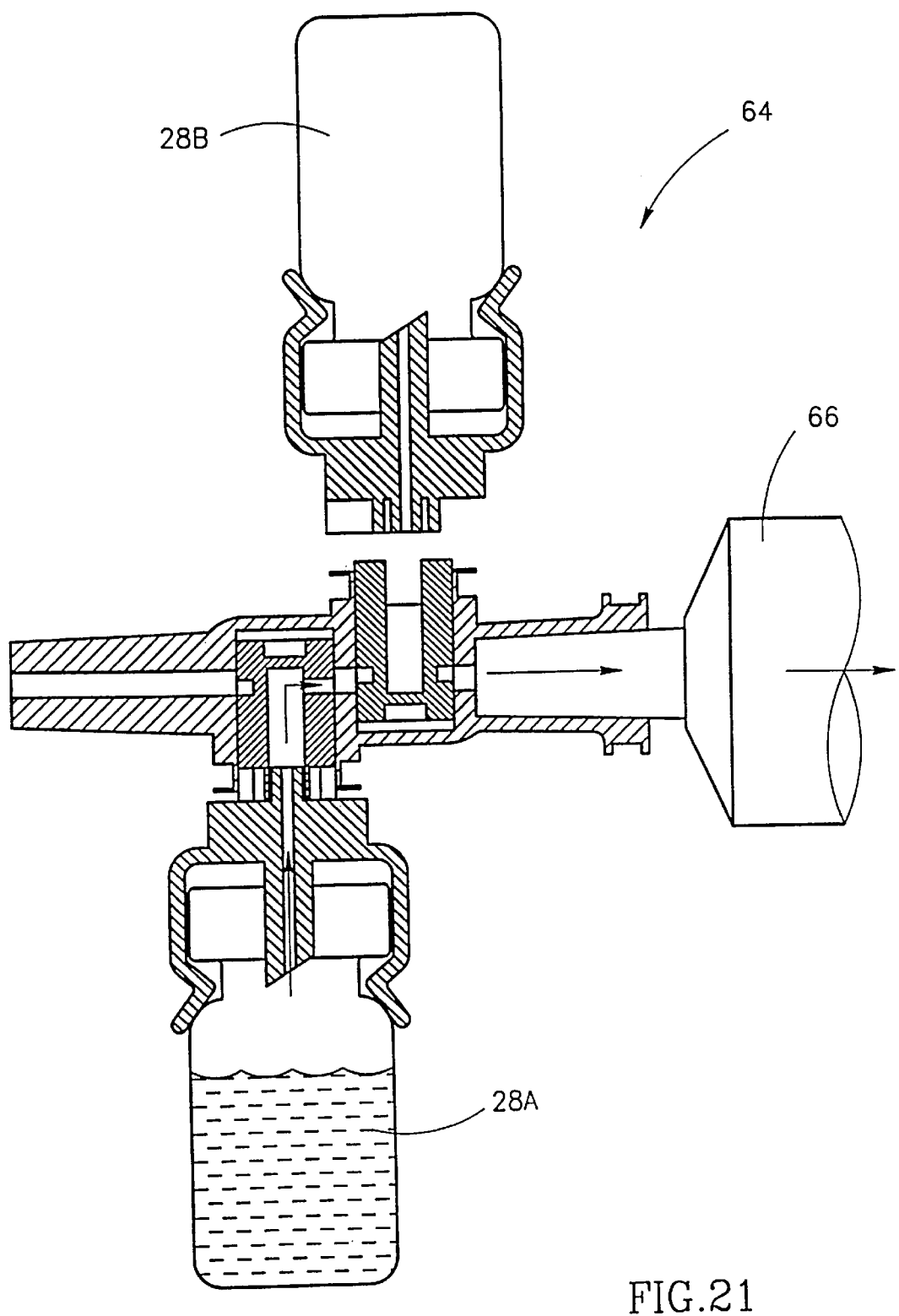
FIG. 21 is a vertical cross sectional view of the fluid control device of FIG. 20 in a second operative position enabling flow communication between the vial containing the reconstituted drug and a syringe.
Figure 22:
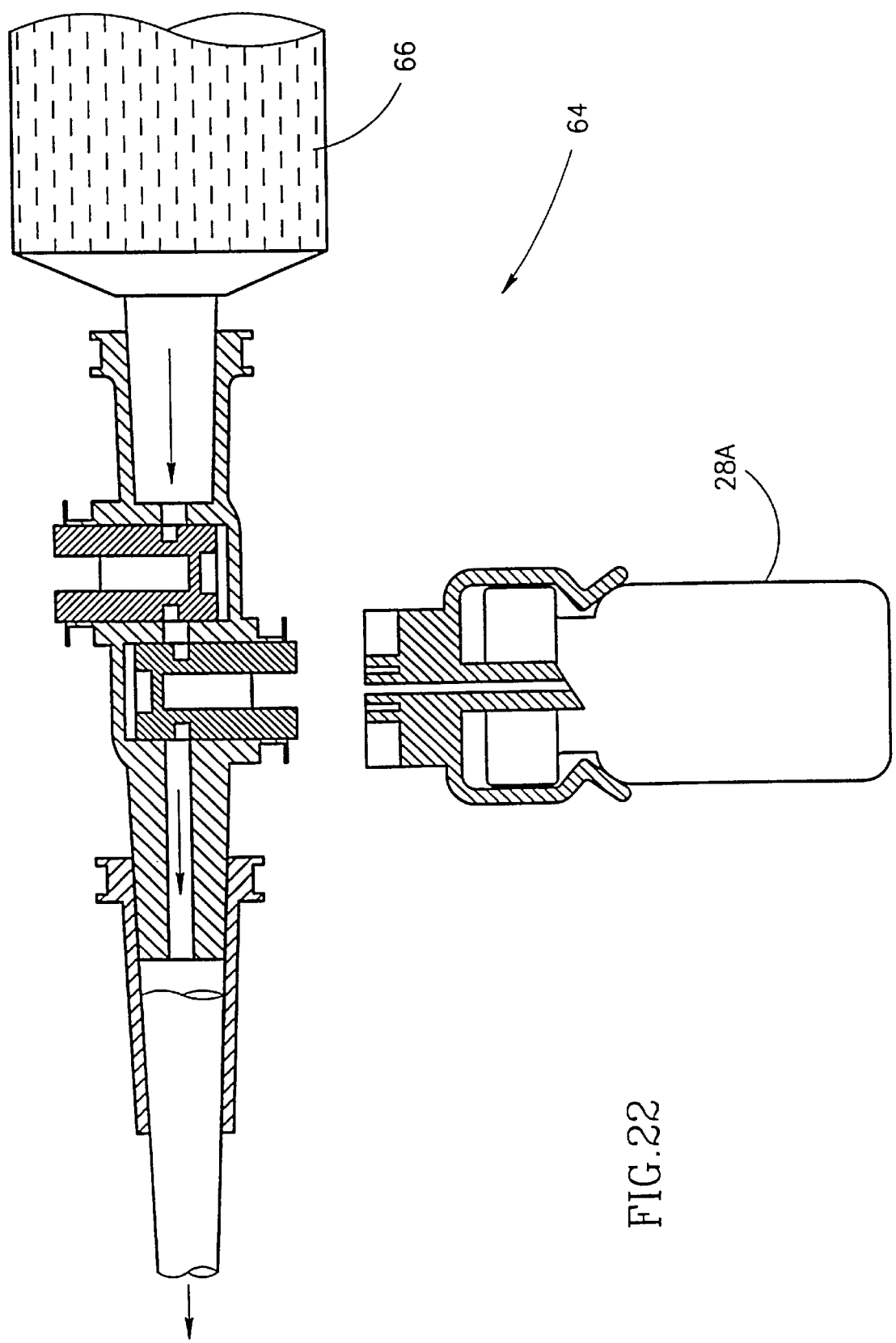
FIG. 22 is a vertical cross sectional view of the fluid control device of FIG. 20 in a third operative position enabling flow communication between the syringe and a dispensing port.

FIGS. 20–22 depict a fluid control device, generally designated 64, for enabling the reconstitution of a powder drug with a physiological solution contained in a medicinal vessel instead of within a pre-filled syringe as required with the fluid control device 10. The fluid control device 64 is similar in construction and operation to the fluid control device 41 and therefore the same reference numerals are used where appropriate.

The main difference between the two fluid control devices 64 and 41 resides in the fact that the former is adapted to be fitted with two medicinal vessels and, as such, its base member 11 is provided with a port 12, a dispensing port 13 and two bores 17A and 17B which are interconnected by a channel 65. As shown, the medicinal vessels are vials 28A and 28B where the vial 28A contains the powdered drug and the vial 28B contains the physiological solution for diluting the powdered drug. As explained in greater detail hereinbelow for the case when the vial 28A has its contents under a high vacuum, the sequence and order of the attachment of the vials 28A and 28B to the adapters 41A and 41B is not arbitrary.

In this case, the flow control member 42A has a first flow control position in which its L-shaped flow duct 23A registers in flow communication with the channel 65 and a medicinal vessel attached to its adaptor 41A (see FIGS. 20 and 21) and a second flow control position in which its peripheral groove flow duct 25A registers in flow communication with the channel 65 and the dispensing port 13 (see FIG. 22). In contrast, the flow control member 42B has a first flow control position in which its L-shaped flow duct 23B registers in flow communication with the channel 65 and a medicinal vessel attached to its adaptor 41B (see FIG. 20) and a second flow control position in which its peripheral groove flow duct 25B registers in flow communication with the channel 65 and the port 12 (see FIGS. 21 and 22).

The operation of the fluid control device 64 for the administration of a powder drug provided in the pressurized vial 28A after reconstitution with a physiological solution provided in the vial 28B is now described. First, as shown in FIG. 20, the fluid control device 64 is provided in its first operative position, namely, enabling the flow path between the vials 28A and 28B when they are attached to the base member 11. It should be noted that the vial 28B is attached to the adaptor 41B and thereafter the pressurized vial 28A is attached to the adaptor 41A such that the physiological solution contents of the vial 41B is sucked into the vial 28A. Reconstitution typically requires shaking the fluid control device 64. As shown in FIG. 21, the adaptor 41B together with the vial 28B are then rotated so as to enable their detachment from the base member 11 whilst, at the same time, effecting the rotation of the flow control member 42B so as to enable a flow path between the port 12 and the remaining vial 28 A. A syringe 66 is inserted into the port 12 and, after inversion of the fluid control device 64 such that the vial 28 containing the reconstituted drug assumes an upward position, the syringe 66 is aspirated to draw the contents of the vial 28A thereinto. Thereafter, as shown in FIG. 22, the adaptor 41A together with the vial 28A are rotated so as to enable their detachment from the base member 11 while, at the same time, effecting the rotation of the flow control member 42A so as to enable a flow path between the syringe 66 and the dispensing port 13. Finally, in this position, the syringe 66 is actuated so as to express the drug for its administration to a patient via the dispensing port 13.

Figure 23:
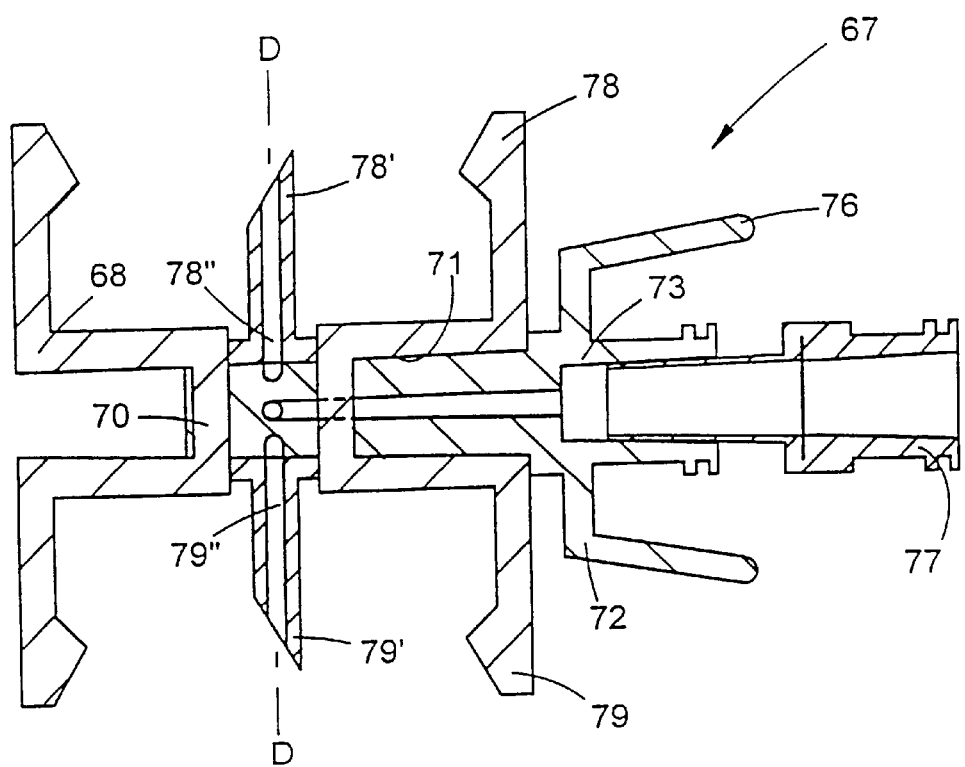
FIG. 23 is a longitudinal cross sectional view of a fluid control device for use with a syringe and a pair of medicinal vessels.
Figure 24:
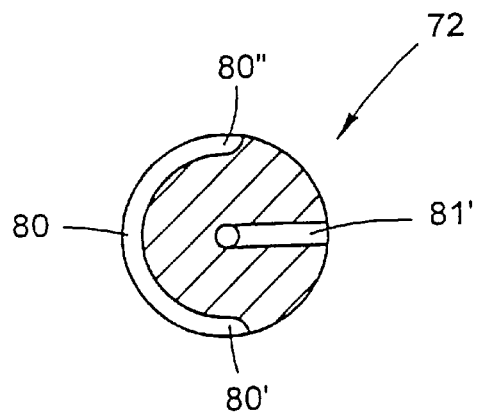
FIG. 24 is a horizontal cross sectional view of the flow control member of the fluid control device of FIG. 23 along line D—D.

FIGS. 23–25 depicts a fluid control device 67 allowing the preparation of a drug by the mixing between a first substance contained in a first medicinal vessel and a second substance contained in a second medicinal vessel and thereafter the transfer of the drug to a dispensing tool, namely, a syringe. The fluid control device 67 includes a base member 68 having a generally tubular intermediate portion 70 defining a lumen 71 in which a flow control member 72 is rotatably inserted. The flow control member 72 has a port 73 for receiving a dispensing tool, typically, a syringe 74 (see FIG. 25). The port 73 is preferably fashioned as a female Luer connector. The flow control member 72 also has integrally formed handles 76 for enabling a manual rotating thereof. As shown, a filter 77 can also be deployed within the port 73 for filtering a drug on its aspiration into a syringe 74.

The base member 68 includes two adapters 78 and 79 which are adapted for the attachment thereto of medicinal vessels. In this case, the adapters 78 and 79 are adapted for the attachment thereto of vials and, as such, they include respective co-axial fluid conduit members 78' and 79' fashioned as piercing tools for puncturing the vials' rubber stoppers. The fluid conduit members 78' and 79' have respective internal apertures 78" and 79".

The flow control member 72 is rotatably mounted for enabling either, in a first flow control position, a flow path between vials attached to the adapters 78 and 79 or, in a second flow control position, a flow path between a syringe and one of the vials. As such, in a similar manner to the flow control member 20' (see FIGS. 3 and 4), flow control member 72 includes two flow ducts as follows: A first flow duct 80 in the form of a peripheral groove slightly longer than semi-circular having end portions 80' and 80" for registration with the interior apertures 78" and 79" so as to enable a flow path between the interiors of vials when attached to the adapters 78 and 79. And a second flow duct 82 in the form of an L-shaped channel having a radial aperture 82' for registration with the interior opening 71' and an axial outlet port 82" so as to enable a flow path between a vial attached to one of the adapters 78 and 79 and a syringe inserted in the port 77.

The operation of the fluid control device 67 is now described with reference to the steps depicted in FIG. 25 for the case that a vial 83 contains a dried drug, e.g. a powder, a crystalline material, a lyophilizate, etc., stored under a high vacuum and a vial 84 contains a physiological solution. As explained in greater detail hereinbelow for the case when the vial 83 has its contents under a high vacuum, the sequence of attachment of the vials 83 and 84 to the adapters 78 and 79 is not arbitrary.

Figure 25D:
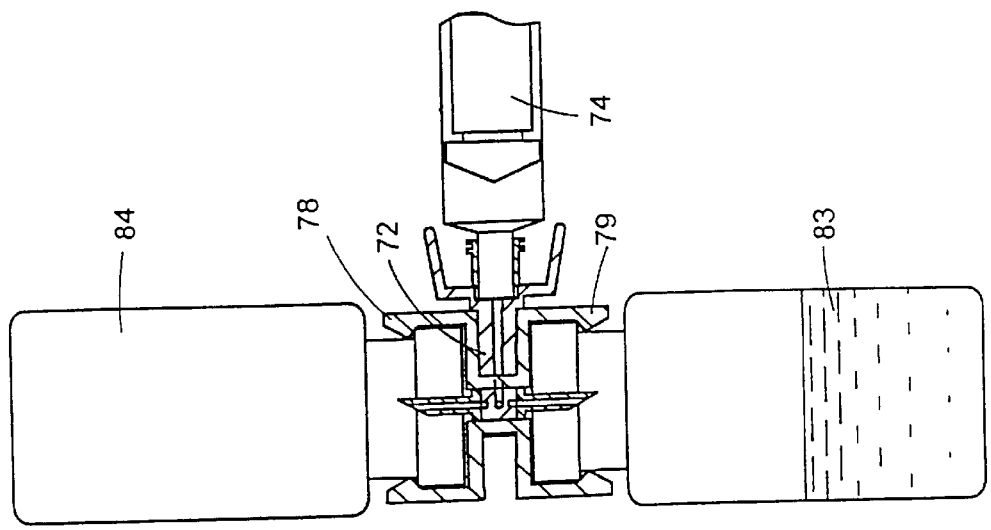
FIG. 25 shows a series of steps (FIGS. 25A–25F) depicting the operation of the fluid control device of FIG. 23.
Figure 25C:
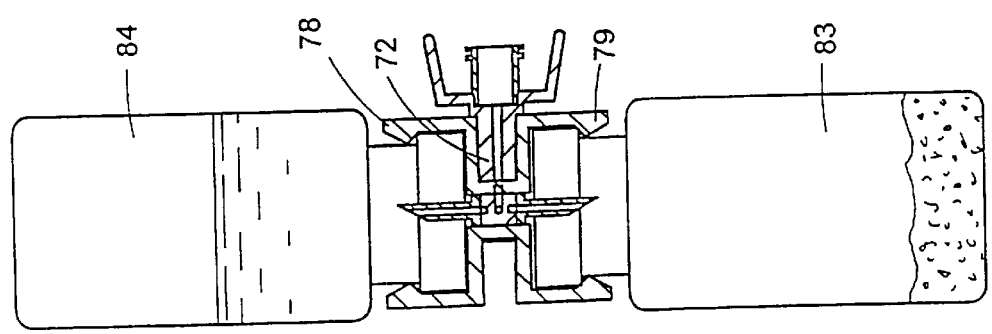
Figure 25B:
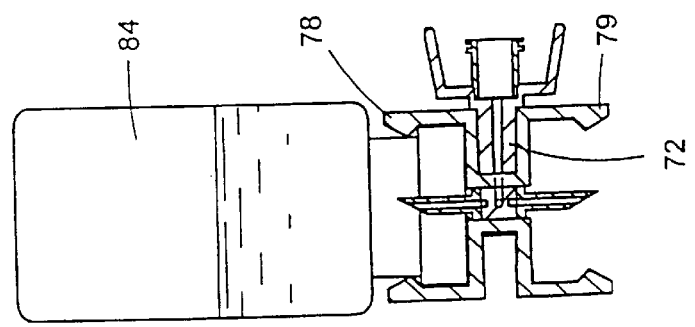
Figure 25A:
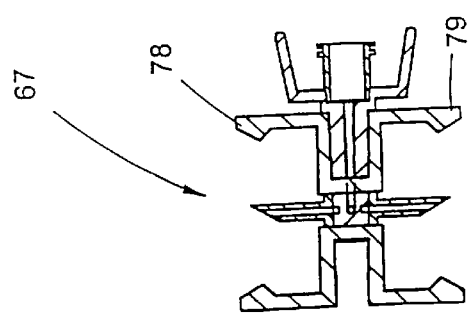

The fluid control device 67 is typically provided in a hermetically sealed package with its flow control member 72 set so as to enable the flow path between flow conduit members 78' and 79' by means of the ends 80' and 80" of its semi-circular groove 80 registering with their interior openings 78" and 79" (FIG. 25A). The vial 84 containing the diluent solution is attached to the adaptor 78 (FIG. 25B), the action of attachment puncturing its rubber stopper and thereafter the vial 83 containing the dried drug is attached to the adaptor 79 (FIG. 25C) thereby sucking the diluent solution thereinto once its rubber stopper is punctured (FIG. 25D). The contents of the vial 83 are then shaken so as to mix the diluent solution with the dried drug.

The syringe 74 is inserted into the port 73 (FIG. 25D) and the flow control member 72 is rotated through a quarter turn relative to the base member 11 such that the flow path between the syringe 74 and the vial 83 is enabled (FIG. 25E). The fluid control device 67 is then inverted (FIG. 25F) and the syringe 74 is aspirated so as to draw the reconstituted drug thereinto, the medicinal preparation passing through a deployed filter 77, if any, thereby becoming particle free for administration to a patient.

Figure 26:
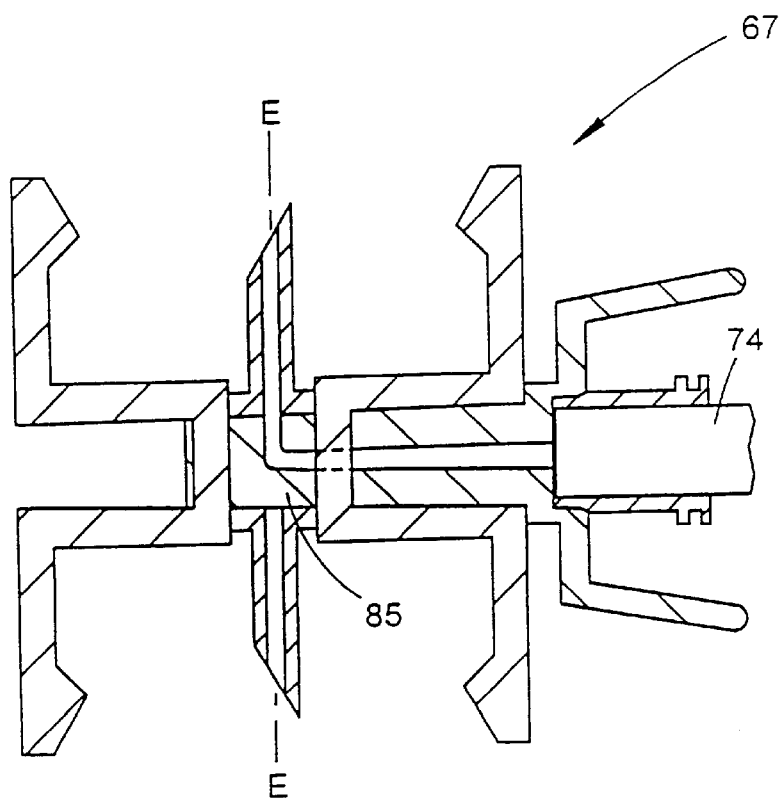
FIG. 26 is a longitudinal cross sectional view of the fluid control device of FIG. 23 with a modified flow control member.
Figure 27:
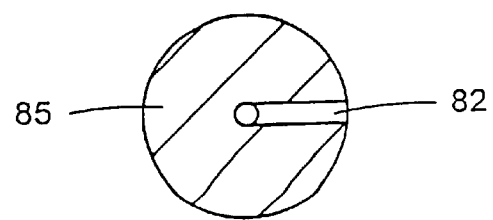
FIG. 27 is a horizontal cross sectional view of the flow control member of FIG. 26 along line E—E in FIG. 26.

FIGS. 26 and 27 depict the fluid control device 67 with a modified flow control member 85 having just the L-shaped flow duct 82, thereby requiring that it be rotated through a 180° turn for switching between its two flow control positions, the first flow control position being between a syringe inserted in the port 73 and a first medicinal vessel whilst the second flow control position being between a syringe inserted in the port 73 and a second medicinal vessel.

The difference between the flow control member 85 and 72 being that a fluid control device 67 fitted with the former can be employed with medicinal vessels in which their contents are under a low vacuum or no vacuum, thereby requiring user intervention to perform he mixing of the powder drug with the physiological solution. In particular, the flow control member 85 is suitable for use with a fluid control device 67 having an adaptor suitable for connection to an IV bag such that on setting the flow control member 85 in its first operative position, the syringe 74 is aspirated so as to introduce a predetermined volume of diluent solution thereinto. Thereafter, on setting the flow control member 85 into its second operative position, the syringe 74 is actuated so as to introduce the diluent solution into a second medicinal vessel containing the drug to be reconstituted. After mixing of the drug with the diluent solution, the syringe 74 is aspirated a second time so as to introduce the medicinal liquid thereinto at which time the syringe 74 is removed for administration of the drug to a patient. In this fashion, such a fluid control device can be used a number of times with one or more medicinal vessels.

Figure 28:
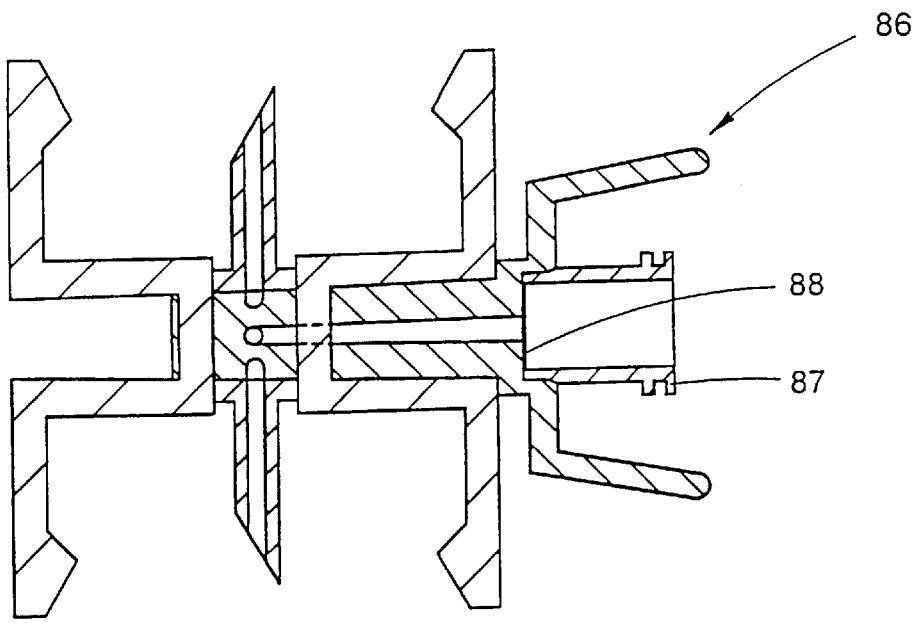
FIG. 28 is a longitudinal cross sectional view of a modified fluid control device of FIG. 23 with an in-line filter.
Figure 29:
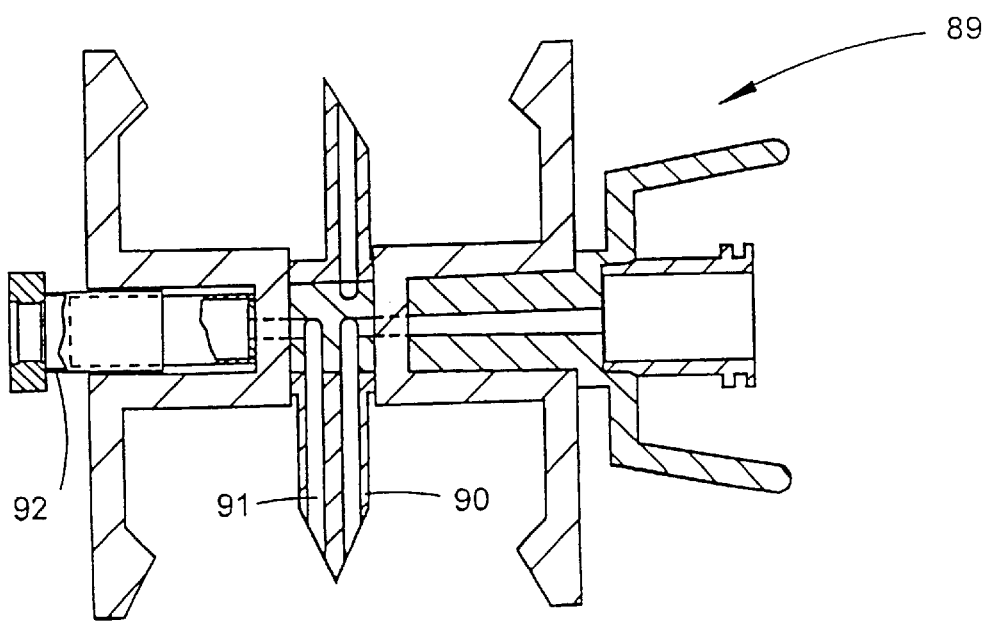
FIG. 29 is a longitudinal cross sectional view of a fluid control device with a modified adaptor enabling venting of a medicinal vessel attached thereto fitted with a hydrophobic filter.

FIG. 28 depicts a fluid control device 86 with a port 87 provided with an integral in-line filter 88, thereby obviating the need for a filter 77. FIG. 29 depicts a fluid control device 89 with a modified adaptor 90 having a vent conduit 91 for venting the vial attached thereto provided with a hydrophobic filter 92 so as to prevent wastage of the mixed drug when the fluid control device 89 is manipulated into the position shown in FIG. 25F.

While the invention has been described with respect to a limited number of embodiments, it will be appreciated that many variations, modifications and other applications of the invention may be made.

What is claimed is:

1. A fluid control device comprising at least a first port; a second port for receiving a syringe; a third port comprising an adaptor having a fluid conduit member extending into an interior of a medicinal vessel attached to said adaptor, and a flow control member displaceable between first and second flow control positions respectively enabling flow paths between first and second pairs of said at least three ports;

wherein one of said second and third ports is coupled to said flow control member and is rotationally displaceable between first and second control positions thereby correspondingly rotating said flow control member between said first and second flow control positions, said flow control member being coupled to said adaptor whereby the flow control member is rotated by rotating the vessel attached to said adaptor.

2. A device according to claim 1, wherein said adaptor is integrally formed with said flow control member, thereby constituting an integrally formed adaptor cum flow control member.

3. A device according to claim 2, wherein said integrally formed adaptor cum flow control member includes a weakened portion enabling a forced non-reversible detachment of said adaptor from said flow control member at the second flow control position.

4. A device according to claim 3, wherein said adaptor is coupled to said flow control member by interengaging means enabling a reversible screw-like detachment of said adapter from said flow control member at the second flow control position.

5. A device according to claim 1, wherein said flow control member is coupled to said second port.

6. A device according to claim 5, wherein said first pair of said at least three ports includes said first and third ports and said second pair of said at least three ports includes said second and third ports.

7. A device according to claim 5, wherein said first pair of said at least three ports includes said first and second ports and said second pair of said at least three ports includes said second and third ports.

8. A device according to claim 5 wherein said second port further comprises an in-line filter.

9. A device according to claim 1 wherein said adapter further comprises a venting conduit extending into the interior of the medicinal vessel.

* * * * *

UNITED STATES PATENT AND TRADEMARK OFFICE
CERTIFICATE OF CORRECTION

PATENT NO. : 6,238,372 B1
DATED : May 29, 2001
INVENTOR(S) : Fredy Zinger et al.

It is certified that error appears in the above-identified patent and that said Letters Patent is hereby corrected as shown below:

<u>Title page,</u>
Insert -- Related U.S. Application Data [63] Continuation-in-part of application No. 08/499,213 filed Jul. 7, 1995, now abandoned, which is a continuation-in-part of application No. 08/407,287 filed Mar. 20, 1995, now abandoned --.

Signed and Sealed this

Nineteenth Day of February, 2002

*Attest:*

JAMES E. ROGAN
*Attesting Officer*     *Director of the United States Patent and Trademark Office*